(12) United States Patent
Babak et al.

(10) Patent No.: US 11,958,869 B2
(45) Date of Patent: Apr. 16, 2024

(54) RUTHENIUM ARENE SCHIFF-BASE COMPLEXES AND USES THEREOF

(71) Applicants: CITY UNIVERSITY OF HONG KONG, Kowloon (HK); NATIONAL UNIVERSITY OF SINGAPORE, Singapore (SG)

(72) Inventors: Maria Babak, Hong Kong (HK); Wee Han Ang, Singapore (SG); Mun Juinn Chow, Singapore (SG)

(73) Assignee: CITY UNIVERSITY OF HONG KONG, Kowloon (HK)

( * ) Notice: Subject to any disclaimer, the term of this patent is extended or adjusted under 35 U.S.C. 154(b) by 0 days.

(21) Appl. No.: 17/720,110

(22) Filed: Apr. 13, 2022

(65) Prior Publication Data
US 2022/0348601 A1  Nov. 3, 2022

Related U.S. Application Data

(60) Provisional application No. 63/174,425, filed on Apr. 13, 2021.

(51) Int. Cl.
*A61P 35/00* (2006.01)
*C07F 15/00* (2006.01)

(52) U.S. Cl.
CPC .......... *C07F 15/0046* (2013.01); *A61P 35/00* (2018.01)

(58) Field of Classification Search
CPC .............................. C07F 15/0046; A61P 35/00
See application file for complete search history.

(56) References Cited

PUBLICATIONS

Chow et al., 57(14) J. Med. Chem. 6043-6059 (2014) (Year: 2014).*
Chow et al., 13 Mol. Pharmaceutics 2543-2554 (2016) (Year: 2016).*
Chow et al., 15 Mol. Pharmaceutics 3020-3031 (2018) (Year: 2018).*

* cited by examiner

Primary Examiner — Timothy R Rozof
(74) Attorney, Agent, or Firm — Conley Rose, P.C.; Michael W. Piper; Andrew M. Metrailer

(57) ABSTRACT

Disclosed herein are ruthenium arene Schiff-base complex and uses thereof. The ruthenium arene Schiff-base complex disclosed herein has the structure of formula (I),

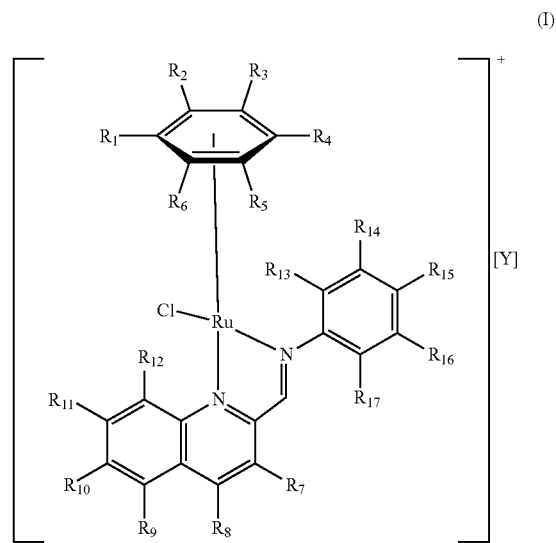

wherein, $R_1$, $R_2$, $R_3$, $R_4$, $R_5$, $R_6$, $R_7$, $R_8$, $R_9$, $R_{10}$, $R_{11}$, and $R_{12}$ are independently H, alkyl, alkoxyl, or halo; $R_{13}$, $R_{14}$, $R_{15}$, $R_{16}$, and $R_{17}$ are independently H, alkyl, alkoxyl, hydroxy, halo, —C(=NH)NH$_2$, —SO$_3$H, —SO$_2$NH$_2$, —NR'R", or —CONH$_2$; or $R_{13}$ and $R_{14}$ are taken together to form a benzene ring, while $R_{15}$, $R_{16}$, and $R_{17}$ are independently H, alkyl, alkoxyl, hydroxy, halo, —C(=NH)NH$_2$, —SO$_3$H, —SO$_2$NH$_2$, —NR'R", or —CONH$_2$; or $R_{14}$ and $R_{15}$ are taken together to form a benzene ring, while $R_{13}$, $R_{16}$, and $R_{17}$ are independently H, alkyl, alkoxyl, hydroxy, halo, —C(=NH)NH$_2$, —SO$_3$H, —SO$_2$NH$_2$, —NR'R", or —CONH$_2$; R' and R" are independently H or alkyl; the alkyl is optionally substituted with one or more halo or hydroxy, or hydroxy; and Y is a counter anion. Also disclosed herein are methods of treating malignant neoplasm in a subject. The method includes administering an effective amount of the ruthenium arene Schiff-base complex of formula (I) to the subject to alleviate symptoms associated with the malignant neoplasm. Exemplary malignant neoplasm includes, but is not limited to triple-negative breast cancer.

9 Claims, 8 Drawing Sheets

RUTHENIUM ARENE SCHIFF-BASE COMPLEXES AND USES THEREOF

CROSS REFERENCES TO RELATED APPLICATION

This application claims priority to U.S. Provisional Patent Application Ser. No. 63/174,425, filed Apr. 13, 2021, the content of which is incorporated herein by reference in its entirety.

BACKGROUND OF THE INVENTION

1. Field of the Invention

The present disclosure in general relates to the field of cancer treatment; more particularly to novel ruthenium arene Schiff-base complexes, and their uses in the treatment and/or prophylaxis of malignant neoplasm.

2. Description of Related Art

Cancer is the second leading cause of death in economically developed countries. Platinum-based anti-cancer drugs have been in clinical use for cancer treatment for over 40 years, to date, cisplatin and its analogues are some of the most effective chemotherapeutic agents in clinical use. However, platinum-based drugs are not without problems. Their high toxicity and incidence of drug resistance remain the main challenge in their clinical application.

In the search of anti-cancer agents containing metals other than platinum, ruthenium compounds turn out to be the most promising ones. The ligand exchange kinetics of metal complexes in aqueous solution are very similar for platinum (II) and ruthenium (II) complexes. Ruthenium thus has been considered to be attractive alternative to platinum, in particular since many ruthenium compounds are not toxic to cells, or are quite selective for cancer cells.

Inventors of this disclosure have identified some ruthenium-based complexes that suppress the growth and/or invasive properties of mammospheres of cancer cells. Accordingly, these ruthenium-based complexes may serve as candidates for the development of medicaments for the treatment and/or prophylaxes of cancers.

SUMMARY

Accordingly, one aspect of the present disclosure is to provide a ruthenium arene Schiff-base complex having the structure of formula (I), a solvate or a stereoisomer thereof,

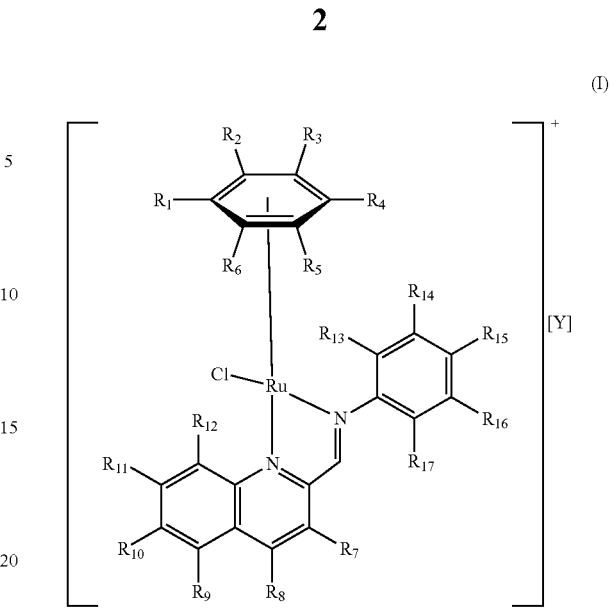

(I)

wherein, $R_1$, $R_2$, $R_3$, $R_4$, $R_5$, $R_6$, $R_7$, $R_8$, $R_9$, $R_{10}$, $R_{11}$, and $R_{12}$ are independently H, alkyl, alkoxyl, or halo;

$R_{13}$, $R_{14}$, $R_{15}$, $R_{16}$, and $R_{17}$ are independently H, alkyl, alkoxyl, hydroxy, halo, —C(=NH)NH$_2$, —SO$_3$H, —SO$_2$NH$_2$, —NR'R", or —CONH$_2$; or $R_{13}$ and $R_{14}$ are taken together to form a benzene ring, while $R_{15}$, $R_{16}$, and $R_{17}$ are independently H, alkyl, alkoxyl, hydroxy, halo, —C(=NH)NH$_2$, —SO$_3$H, —SO$_2$NH$_2$, —NR'R", or —CONH$_2$; or $R_{14}$ and $R_{15}$ are taken together to form a benzene ring, while $R_{13}$, $R_{16}$, and $R_{17}$ are independently H, alkyl, alkoxyl, hydroxy, halo, —C(=NH)NH$_2$, —SO$_3$H, —SO$_2$NH$_2$, —NR'R", or —CONH$_2$;

R' and R" are independently H or alkyl;

the alkyl is optionally substituted with one or more halo or hydroxy; and

Y is a counter anion.

Examples of the counter anion of the compound of formula (I) include, but are not limited to, chloride, bromide, iodine, acetate, ascorbate, benzoate, benzenesulfonate, butyrate, cyclopentanepropionate, dodecylsulfoate, ethanesulfonate, glucuronate, glucoheptonate, hemisulfate, heptonate, hexonate, 2-hydroxyethanesulfonate, lactate, laurate, lauryl sulfate, methanesulfonate, 2-naphthalenesulfonate, nicotinate, nitrate, oleate, palmitate, 3-phenylpropionate, picrate, pivalate, propionate, stearate, thiocyanate, toluenesulfonate, trifluoroacetate, tosylate, undecanoate, valerate, and the like. According to some preferred embodiments of the present disclosure, the counter anion of the compound of formula (I) is chloride.

According to one preferred embodiment of the present disclosure, in the compound of formula (I), $R_2$, $R_4$, and $R_6$ are independently isopropyl; $R_1$, $R_3$, $R_5$, $R_7$, $R_8$, $R_9$, $R_{10}$, $R_{11}$, $R_{12}$, $R_{13}$, $R_{14}$, $R_{16}$ and $R_{17}$ are independently H; $R_{15}$ is methoxy; and Y is chloride (i. e., [(η6-1,3, 5-triisopropybenzene)RuCl(4-methoxy-N-(2-quinolinyl-methylene)-aniline)].

According to another preferred embodiment of the present disclosure, in the compound of formula (I), $R_1$, $R_2$, $R_3$, $R_4$, $R_5$, and $R_6$ are independently methyl; $R_7$, $R_8$, $R_9$, $R_{10}$, $R_{11}$, $R_{12}$, $R_{13}$, $R_{14}$, $R_{16}$ and $R_{17}$ are independently H; $R_{15}$ is methoxy; and Y is chloride (i.e., [(η6-hexamethylbenzene)RuCl(4-methoxy-N-(2-quinolinyl-methylene)-aniline)]Cl).

According to still another preferred embodiment of the present disclosure, in the compound of formula (I), $R_2$, $R_4$, and $R_6$ are independently isopropyl; $R_1$, $R_3$, $R_5$, $R_7$, $R_8$, $R_9$, $R_{10}$, $R_{11}$, $R_{12}$, $R_{13}$, $R_{14}$, $R_{15}$, and $R_{17}$ are independently H; $R_{16}$ is chloro; and Y is chloride (i.e., [(η6-1,3,5-triisopropybenzene)RuCl(3-chloro-N-(2-quinolinylmethylene)-aniline)].

According to a further preferred embodiment of the present disclosure, in the compound of formula (I), $R_1$, $R_2$, $R_3$, $R_4$, $R_5$, and $R_6$ are independently methyl; $R_7$, $R_8$, $R_9$, $R_{10}$, $R_{11}$, $R_{12}$, $R_{13}$, $R_{14}$, $R_{15}$ and $R_{17}$ are independently H; $R_{16}$ is chloro; and Y is chloride (i.e., [(η6-Hexamethylbenzene)RuCl(3-chloro-N-(2-quinolinylmethylene)aniline)].

The second aspect of the present disclosure is to provide a pharmaceutical composition for the treatment and/or prophylaxis of a subject having a malignant neoplasm. The pharmaceutical composition comprises the compound of formula (I), a solvate or a stereoisomer thereof; and a pharmaceutically acceptable carrier.

The compound of formula (I) is present at a level of about 0.1% to 99% by weight, based on the total weight of the pharmaceutical composition. In some embodiments, the compound of formula (I) is present at a level of at least 1% by weight, based on the total weight of the pharmaceutical composition. In certain embodiments, the compound of formula (I) is present at a level of at least 5% by weight, based on the total weight of the pharmaceutical composition. In still other embodiments, the compound of formula (I) is present at a level of at least 10% by weight, based on the total weight of the pharmaceutical composition. In still yet other embodiments, the compound of formula (I) is present at a level of at least 25% by weight, based on the total weight of the pharmaceutical composition.

Preferably, in the compound of formula (I), $R_2$, $R_4$, and $R_6$ are independently isopropyl; $R_1$, $R_3$, $R_5$, $R_7$, $R_8$, $R_9$, $R_{10}$, $R_{11}$, $R_{12}$, $R_{13}$, $R_{14}$, $R_{16}$ and $R_{17}$ are independently H; $R_{15}$ is methoxy; and Y is chloride (i.e., [(η6-1,3,5-triisopropybenzene)RuCl(4-methoxy-N-(2-quinolinyl-methylene)-aniline)]Cl).

According to another preferred embodiment of the present disclosure, in the compound of formula (I), $R_1$, $R_2$, $R_3$, $R_4$, $R_5$, and $R_6$ are independently methyl; $R_7$, $R_8$, $R_9$, $R_{10}$, $R_{11}$, $R_{12}$, $R_{13}$, $R_{14}$, $R_{16}$ and $R_{17}$ are independently H; $R_{15}$ is methoxy; and Y is chloride (i.e., [(η6-hexamethylbenzene)RuCl(4-methoxy-N-(2-quinolinyl-methylene)-aniline)]Cl).

According to still another preferred embodiment of the present disclosure, in the compound of formula (I), $R_2$, $R_4$, and $R_6$ are independently isopropyl; $R_1$, $R_3$, $R_5$, $R_7$, $R_8$, $R_9$, $R_{10}$, $R_{11}$, $R_{12}$, $R_{13}$, $R_{14}$, $R_{15}$, and $R_{17}$ are independently H; $R_{16}$ is chloro; and Y is chloride (i.e., [(η6-1,3,5-triisopropybenzene)RuCl(3-chloro-N-(2-quinolinylmethylene)-aniline)].

According to a further preferred embodiment of the present disclosure, in the compound of formula (I), $R_1$, $R_2$, $R_3$, $R_4$, $R_5$, and $R_6$ are independently methyl; $R_7$, $R_8$, $R_9$, $R_{10}$, $R_{11}$, $R_{12}$, $R_{13}$, $R_{14}$, $R_{15}$ and $R_{17}$ are independently H; $R_{16}$ is chloro; and Y is chloride (i.e., [(η6-Hexamethylbenzene)RuCl(3-chloro-N-(2-quinolinylmethylene)aniline)]Cl).

The pharmaceutical composition of the present disclosure may be administered to the subject via intravascular delivery (e.g., injection or infusion), oral, enteral, rectal, pulmonary (e.g., inhalation), nasal, topical (including transdermal, buccal and sublingual), intravesical, intravitreal, subconjunctival, intraperitoneal, vaginal, brain delivery (e.g., intra-cerebroventricular, and intracerebral), CNS delivery (e.g., intrathecal, perispinal, and intra-spinal) or parenteral (e.g., subcutaneous, intramuscular, intravenous, and intradermal), transmucosal administration or administration via an implant, or other delivery routes known in the art.

The present disclosure also encompasses a method for the treatment or prophylaxis of a subject having a malignant neoplasm. The method comprises administering to the subject a therapeutically or prophylactically effective amount of the present pharmaceutical composition.

Examples of the malignant neoplasm treatable by the present method include but are not limited to, carcinoma, sarcoma, lymphoma, leukemia, germ cell tumor, blastoma, brain cancer, medulloblastoma, glioma, head and neck cancer, oral cancer, laryngeal cancer, nasopharynx cancer, thyroid cancer, myeloid neoplasm, lung cancer, non-small cell lung cancer, small cell lung cancer, mesothelioma, hepatocellular carcinoma, lymphoid neoplasm, bone cancer, Ewing sarcoma, osteosarcoma, skeletal cancer, muscle cancer, rhabdomyosarcoma, skin cancer, basal cell carcinoma, squamous cell carcinoma, connective tissue cancer, fibrosarcoma, cartilage cancer, chondrosarcoma, nerve tissue cancer, neuroblastoma, gastric cancer, esophageal cancer, pancreatic cancer, kidney cancer, bladder cancer, prostate cancer, breast cancer, triple-negative breast cancer, testicular cancer, ovarian cancer, uterine cancer, fallopian tube cancer, and cervical cancer.

According to some embodiments of the present disclosure, the subject has the breast cancer. In one preferred embodiment, the breast cancer is a triple-negative breast cancer.

According to some embodiments of the present disclosure, the breast cancer is resistant to a hormone-based chemotherapeutic agent, an antibody-based chemotherapeutic agent, a platinum-based chemotherapeutic agent or a combination thereof.

According to further embodiments of the present disclosure, the malignant neoplasm is a metastatic malignant neoplasm.

In all embodiments, the subject is a human.

In preferred embodiments, the synthetic peptide of the present disclosure is administered in an amount of 0.0001-50 mg/Kg to the subject.

The details of one or more embodiments of this disclosure are set forth in the accompanying description below. Other features and advantages of the invention will be apparent from the detail descriptions, and from claims.

It is to be understood that both the foregoing general description and the following detailed description are by examples, and are intended to provide further explanation of the invention as claimed.

BRIEF DESCRIPTION OF THE DRAWINGS

The accompanying drawings, which are incorporated in and constitute a part of the specification, illustrate various example systems, methods and other exemplified embodiments of various aspects of the invention. The present description will be better understood from the following detailed description read in light of the accompanying drawings, where.

DETAILED DESCRIPTION OF THE PREFERRED EMBODIMENTS

Figure 1:
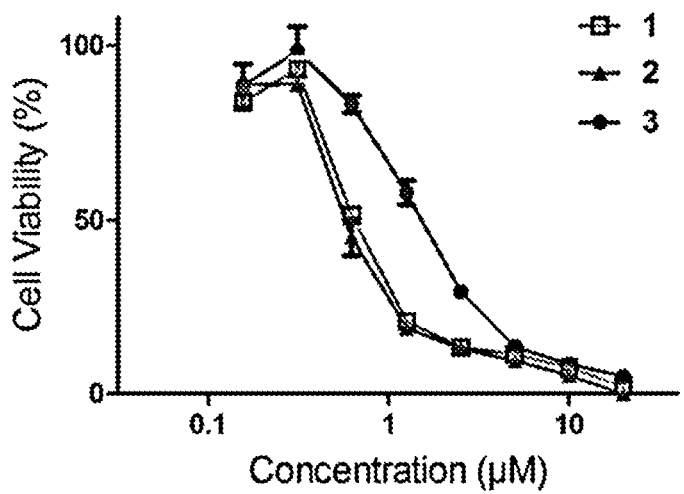
FIG. 1 is a line graph depicting the dose-response curves of the compounds 1, 2 and 3 on MDA-MB-231 mammospheres in accordance with one embodiment of the present disclosure.

The detailed description provided below in connection with the appended drawings is intended as a description of the present disclosure and is not intended to represent the only forms in which the present disclosure may be constructed or utilized.

1. Definitions

For convenience, certain terms employed in the context of the present disclosure are collected here. Unless defined otherwise, all technical and scientific terms used herein have the same meaning as commonly understood by one of the ordinary skill in the art to which this invention belongs.

Unless otherwise indicated, the term "alkyl" herein refers to a straight or branched hydrocarbon group, containing 1-20 (e.g., 1-8 and 1-5) carbon atoms. Examples include methyl, ethyl, n-propyl, i-propyl, n-butyl, i-butyl, and t-butyl.

The term "alkoxy" refers to an —O-alkyl group. Examples include methoxy, ethoxy, propoxy, isopropoxy, and the like.

The term "halo" refers to a fluoro, chloro, bromo, or iodo radical.

Alkyl and alkoxy mentioned herein include both substituted and unsubstituted moieties. Examples of substituents include, but are not limited to, halo, hydroxyl, amino, cyano, nitro, mercapto, alkoxycarbonyl, amido, carboxy, alkanesulfonyl, alkylcarbonyl, carbamido, carbamyl, carboxyl, thioureido, thiocyanato, sulfonamido, alkyl, alkenyl, alkynyl, alkyloxy, aryl, heteroaryl, cycloalkyl, and heterocloalkyl, in which alkyl, alkenyl, alkynyl, alkyloxy, aryl, heteroaryl, cycloalkyl, and heterocycloalkyl may further be substituted.

Herein, the term "compound" refers to the ruthenium arene Schiff-base complex of Formula (I) described above, as well as their solvates or stereoisomers, if applicable. A "solvate" refers to a complex formed between an active compound and a pharmaceutically acceptable solvent, usually by a solvolysis reaction. This physical association may include hydrogen bonding. Examples of a pharmaceutically acceptable solvent include water, ethanol, isopropanol, ethyl acetate, acetic acid, ethanolamine, dimethyl sulfoxide (DMSO), tetrahydrofuran (THF), diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates.

It should also be noted that if the stereochemistry of a structure or a portion of a structure is not indicated with, for example, bold or dashed lines, the structure or the portion of the structure is to be interpreted as encompassing all stereoisomers of it. Similarly, names of compounds having one or more chiral centers that do not specify the stereochemistry of those centers encompass pure stereoisomers and mixtures thereof. Moreover, any atom shown in a drawing with unsatisfied valences is assumed to be attached to enough hydrogen atoms to satisfy the valences.

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "triple negative breast cancer (TNBC)" as used herein refers to a kind of breast cancer that has reduced or negligible expression of receptors that are commonly found in breast cancer, such as estrogen receptor (ER), progesterone receptor (PR), and HER-2. HER-2 may be known by other names, e.g., HER2/neu or ERBB2. The TNBC phenotype may be referred to as ER-/PR-/HER2-. The reduced or lack of expression of such receptors may be determined by any suitable methods known in the art, for example, by anti-receptor antibody, genotyping and the like.

Unless otherwise indicated, a "therapeutically effective amount" of a compound is an amount sufficient to provide a therapeutic benefit in the treatment or management of a disease or condition, or to delay or minimize one or more symptoms associated with the disease or condition. A therapeutically effective amount of a compound is an amount of therapeutic agent, alone or in combination with other therapies, which provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent.

Unless otherwise indicated, a "prophylactically effective amount" of a compound is an amount sufficient to prevent a disease or condition, or one or more symptoms associated with the disease or condition, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

Unless otherwise indicated, the terms "treat," "treating" and "treatment" contemplate an action that occurs while a patient is suffering from the specified disease or disorder, which reduces the severity of the disease or disorder, or one or more of its symptoms, or retards or slows the progression of the disease or disorder.

The term "subject" or "patient" is used interchangeably herein and is intended to mean a mammal including the human species that is susceptible to infection by a virus. The term "mammal" refers to all members of the class Mammalia, including humans, primates, domestic and farm animals, such as rabbit, pig, sheep, and cattle; as well as zoo, sports or pet animals, such as mouse and rat. Further, the term "subject" or "patient" intended to refer to both the male and female gender unless one gender is specifically indicated. Accordingly, the term "subject" or "patient" comprises any mammal which may benefit from the treatment method of the present disclosure. Examples of a "subject" or "patient" include, but are not limited to, a human, rat, mouse, guinea pig, monkey, pig, goat, cow, horse, dog, cat, bird, and fowl. In a preferred embodiment, the subject is a human.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The singular forms "a", "and", and "the" are used herein to include plural referents unless the context clearly dictates otherwise.

2. Detail Description of Preferred Embodiments

The present disclosure is based, at least in part, on the discovery of some ruthenium arene Schiff-base complexes are capable of suppressing the growth of mammospheres of cancer cells, thus they are potential candidates for the development of medicaments for the treatment and/or prophylaxis of cancers. Accordingly, this invention provides method and composition comprising the newly identified ruthenium arene Schiff-base complexes for the treatment and/or prophylaxis of a malignant neoplasm.

2.1 The Ruthenium Arene Schiff-Base Complex

The present ruthenium arene Schiff-base complex has the structure of formula (I),

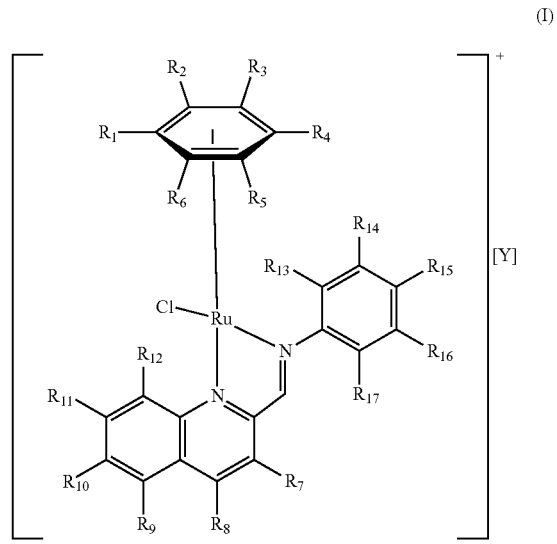

wherein, $R_1$, $R_2$, $R_3$, $R_4$, $R_5$, $R_6$, $R_7$, $R_8$, $R_9$, $R_{10}$, $R_{11}$, and $R_{12}$ are independently H, alkyl, alkoxyl, or halo;

$R_{13}$, $R_{14}$, $R_{15}$, $R_{16}$, and $R_{17}$ are independently H, alkyl, alkoxyl, hydroxy, halo, —C(=NH)NH$_2$, —SO$_3$H, —SO$_2$NH$_2$, —NR'R", or —CONH$_2$; or $R_{13}$ and $R_{14}$ are taken together to form a benzene ring, while $R_{15}$, $R_{16}$, and $R_{17}$ are independently H, alkyl, alkoxyl, hydroxy, halo, —C(=NH)NH$_2$, —SO$_3$H, —SO$_2$NH$_2$, —NR'R", or —CONH$_2$; or $R_{14}$ and $R_{15}$ are taken together to form a benzene ring, while $R_{13}$, $R_{16}$, and $R_{17}$ are independently H, alkyl, alkoxyl, hydroxy, halo, —C(=NH)NH$_2$, —SO$_3$H, —SO$_2$NH$_2$, —NR'R", or —CONH$_2$;

R' and R" are independently H or alkyl;

the alkyl is optionally substituted with one or more halo or hydroxy; and

Y is a counter anion.

Exemplary counter anion of the compound of formula (I) may be any one of chloride, bromide, iodine, acetate, ascorbate, benzoate, benzenesulfonate, butyrate, cyclopentanepropionate, dodecylsulfoate, ethanesulfonate, glucuronate, glucoheptonate, hemisulfate, heptonate, hexonate, 2-hydroxyethanesulfonate, lactate, laurate, lauryl sulfate, methanesulfonate, 2-naphthalenesulfonate, nicotinate, nitrate, oleate, palmitate, 3-phenylpropionate, picrate, pivalate, propionate, stearate, thiocyanate, toluenesulfonate, trifluoroacetate, tosylate, undecanoate, and valerate. According to certain embodiments, the counter anion of the compound of formula (I) is chloride.

According to one preferred embodiment of the present disclosure, in the compound of formula (I), $R_2$, $R_4$, and $R_6$ are independently isopropyl; $R_1$, $R_3$, $R_5$, $R_7$, $R_8$, $R_9$, $R_{10}$, $R_{11}$, $R_{12}$, $R_{13}$, $R_{14}$, $R_{16}$ and $R_{17}$ are independently H; $R_{15}$ is methoxy; and Y is chloride (i. e., [(η6-1,3,5-triisopropybenzene)RuCl(4-methoxy-N-(2-quinolinyl-methylene)-aniline)]Cl).

According to another preferred embodiment of the present disclosure, in the compound of formula (I), $R_1$, $R_2$, $R_3$, $R_4$, $R_5$, and $R_6$ are independently methyl; $R_7$, $R_8$, $R_9$, $R_{10}$, $R_{11}$, $R_{12}$, $R_{13}$, $R_{14}$, $R_{16}$ and $R_{17}$ are independently H; $R_{15}$ is methoxy; and Y is chloride (i.e., [(η6-hexamethylbenzene)RuCl(4-methoxy-N-(2-quinolinyl-methylene)-aniline)]Cl).

According to still another preferred embodiment of the present disclosure, in the compound of formula (I), $R_2$, $R_4$, and $R_6$ are independently isopropyl; $R_1$, $R_3$, $R_5$, $R_7$, $R_8$, $R_9$, $R_{10}$, $R_{11}$, $R_{12}$, $R_{13}$, $R_{14}$, $R_{15}$, and $R_{17}$ are independently H; $R_{16}$ is chloro; and Y is chloride (i.e., [(η6-1,3,5-triisopropybenzene)RuCl(3-chloro-N-(2-quinolinylmethylene)-aniline)]Cl).

According to a further preferred embodiment of the present disclosure, in the compound of formula (I), $R_1$, $R_2$, $R_3$, $R_4$, $R_5$, and $R_6$ are independently methyl; $R_7$, $R_8$, $R_9$, $R_{10}$, $R_{11}$, $R_{12}$, $R_{13}$, $R_{14}$, $R_{15}$ and $R_{17}$ are independently H; $R_{16}$ is chloro; and Y is chloride (i.e., [(η6-Hexamethylbenzene)RuCl(3-chloro-N-(2-quinolinylmethylene)aniline)]Cl).

Compounds of the invention contain one or more stereocenters, thus can exist as racemic mixtures of enantiomers or mixtures of diastereomers. This invention thus encompasses stereomerically pure forms of such compounds, as well as mixtures of those forms. Stereoisomers may be asymmetrically synthesized or resolved using standard techniques such as crystallization, chromatography, and the use of a resolving agent. One preferred way of separating enantiomers from a racemic mixture is by use of preparative high performance liquid chromatography (HPLC). Alternatively, the racemic may be separated into its enantiomers by reacting with an optically active form of a resolving agent in the presence of a solvent. Depending on the optical form of the resolving agent, one of the two enantiomers is separated out as an insoluble salt with high yield and high optical purity, while the opposite enantiomer remains in the solution.

The present invention thus further encompasses stereoisomeric mixtures of compounds disclosed herein. It also encompasses configurational isomers of compounds disclosed herein (e.g., cis- and trans-isomers), either in admixture or in pure or substantially pure form.

Methods for synthesizing the compounds of formula (I) are well known in the art. For example, the compounds of formula (I) may be synthesized by the methodology as described in Example 1 of the present disclosure. Generally, the compound of formula (I) may be synthesized by first stirring a picoline-2-aldehyde derivative (B) and an aniline derivative (C) in a solvent to form a Schiff-base (imine) intermediate. The intermediate is then dried and mixed with ruthenium arene (A) in another solvent. The reaction product is then dried and purified to give the desired ruthenium arene Schiff-base complex (D). A person of ordinary skill in the art would understand the synthesis of desired ruthenium arene Schiff-base complex (D) as described herein may be accomplished by selecting proper substrates A, B, and C.

The ruthenium arene Schiff-base complex (i.e., the compounds of formula (I)) thus prepared can be initially screened using in vitro cytotoxicity assays, e.g., the MTT assay described in Example 2.1 below, for their potency in suppressing the growth of cancer cells. They can be subsequently evaluated using in vitro assay for their efficacy in suppressing the growth of mamospheres of tumor stem cells.

The selected compounds can be further tested to verify their in vivo efficacy in treating cancers (e.g., TNBC). For example, a compound can be administered to a tumor-bearing animal (e.g., a rat) and its therapeutic effects are then assessed. Based on the results, an appropriate dosage range and administration route can be determined.

2.2 Pharmaceutical Composition

The second aspect of the present disclosure is to provide a pharmaceutical composition for the treatment or prophylaxis of a malignant neoplasm. The pharmaceutical composition comprises the ruthenium arene Schiff-base complex of formula (I) described above, a solvate or a stereoisomer thereof; and a pharmaceutically acceptable carrier.

According to one preferred embodiment of the present disclosure, in the compound of formula (I), $R_2$, $R_4$, and $R_6$ are independently isopropyl; $R_1$, $R_3$, $R_5$, $R_7$, $R_8$, $R_9$, $R_{10}$, $R_{11}$, $R_{12}$, $R_{13}$, $R_{14}$, $R_{16}$ and $R_{17}$ are independently H; $R_{15}$ is methoxy; and Y is chloride.

According to another preferred embodiment of the present disclosure, in the compound of formula (I), $R_1$, $R_2$, $R_3$, $R_4$, $R_5$, and $R_6$ are independently methyl; $R_7$, $R_8$, $R_9$, $R_{10}$, $R_{11}$, $R_{12}$, $R_{13}$, $R_{14}$, $R_{16}$ and $R_{17}$ are independently H; $R_{15}$ is methoxy; and Y is chloride.

According to still another preferred embodiment of the present disclosure, in the compound of formula (I), $R_2$, $R_4$, and $R_6$ are independently isopropyl; $R_1$, $R_3$, $R_5$, $R_7$, $R_8$, $R_9$, $R_{10}$, $R_{11}$, $R_{12}$, $R_{13}$, $R_{14}$, $R_{15}$, and $R_{17}$ are independently H; $R_{16}$ is chloro; and Y is chloride.

According to a further preferred embodiment of the present disclosure, in the compound of formula (I), $R_1$, $R_2$, $R_3$, $R_4$, $R_5$, and $R_6$ are independently methyl; $R_7$, $R_8$, $R_9$, $R_{10}$, $R_{11}$, $R_{12}$, $R_{13}$, $R_{14}$, $R_{15}$ and $R_{17}$ are independently H; $R_{16}$ is chloro; and Y is chloride.

In some embodiments, the present compound of formula (I) is formulated with one or more pharmaceutically acceptable carriers to form a pharmaceutical composition according to techniques known to those skilled in the art. The compound of formula (I) is present at a level of about 0.1% to 99% by weight, based on the total weight of the pharmaceutical composition. In some embodiments, the compound of formula (I) is present at a level of at least 1% by weight, based on the total weight of the pharmaceutical composition. In certain embodiments, the compound of formula (I) is present at a level of at least 5% by weight, based on the total weight of the pharmaceutical composition. In still other embodiments, the compound of formula (I) is present at a level of at least 10% by weight, based on the total weight of the pharmaceutical composition. In still yet other embodiments, the compound of formula (I) is present at a level of at least 25% by weight, based on the total weight of the pharmaceutical composition.

Certain pharmaceutical compositions are single unit dosage forms suitable for oral, mucosal (e.g., nasal, sublingual, vaginal, buccal, or rectal), parenteral (e.g., subcutaneous, intravenous, bolus injection, intramuscular, or intra-arterial), or transdermal administration to a patient. Examples of dosage forms include, but are not limited to, tablets; caplets; capsules (e.g., soft elastic gelatin capsules); cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The formulation should suit the mode of administration. For example, oral administration requires enteric coatings to protect the compounds of this invention from degradation within the gastrointestinal tract. Similarly, a formulation may contain ingredients that facilitate delivery of the active ingredient(s) to the site of action. For example, compounds may be administered in liposomal formulations, in order to protect them from degradative enzymes, facilitate transport in circulatory system, and effect delivery across cell membranes to intracellular sites.

Similarly, poorly soluble compounds may be incorporated into liquid dosage forms (and dosage forms suitable for reconstitution) with the aid of solubilizing agents, emulsifiers and surfactants such as, but not limited to, cyclodextrins (e.g., α-cyclodextrin or β-cyclodextrin), and non-aqueous solvents, such as, but not limited to, ethyl alcohol, isopropyl alcohol, ethyl carbonate, ethyl acetate, benzyl alcohol, benzyl benzoate, propylene glycol, 1,3-butylene glycol, dimethyl formamide, dimethyl sulfoxide (DMSO), biocompatible oils (e.g., cottonseed, groundnut, corn, germ, olive, castor, and sesame oils), glycerol, tetrahydrofurfuryl alcohol, polyethylene glycols, fatty acid esters of sorbitan, and mixtures thereof (e.g., DMSO:corn oil), lipids such as egg york phosphatidylcoline (EPC), soybean phosphatidylcholine (SPC), 1,2-dioleoyl-sn-glycero-3-phosphocholine (DOPC), 1,2-distearoyl-sn-glycero-3-phosphocholine (DSPC), cholesterol (CHO), dipalmitoylphosphatidylcholine (DPPC) and PEG-2000. According to one preferred embodiment, the compound of formula (I) (i.e., BO-2590) is incorporated into lipids to form liposomes suitable for oral or parenteral administration.

The composition, shape, and type of a dosage form will vary depending on its use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art.

2.2.1 Oral Dosage Forms

Pharmaceutical compositions of the present invention suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art.

Typical oral dosage forms are prepared by combining the active ingredient(s) in an intimate admixture with at least one excipient according to conventional pharmaceutical compounding techniques. Excipients can take a wide variety of forms depending on the form of preparation desired for administration.

Because of their ease of administration, tablets and capsules represent the most advantageous oral dosage unit forms. If desired, tablets can be coated by standard aqueous or non-aqueous techniques. Such dosage forms can be prepared by conventional methods of pharmacy. In general, pharmaceutical compositions and dosage forms are prepared by uniformly and intimately admixing the active ingredients with liquid carriers, finely divided solid carriers, or both, and then shaping the product into the desired presentation if necessary. Dis-integrants may be incorporated in solid dosage forms to facility rapid dissolution. Lubricants may also be incorporated to facilitate the manufacture of dosage forms (e.g., tablets).

2.2.2 Parenteral Dosage Forms

Parenteral dosage forms can be administered to patients by various routes including, but not limited to, subcutaneous, intravenous (including bolus injection), intramuscular, and intra-arterial. Because their administration typically bypasses patients' natural defenses against contaminants, parenteral dosage forms are specifically sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: water; aqueous vehicles such as, but not limited to, sodium chloride solution, Ringer's solution, and Dextrose; water-miscible vehicles such as, but not limited to, ethyl alcohol, polyethylene glycol, and polypropylene glycol; and non-aqueous vehicles such as, but not limited to, lipids, corn oil, cottonseed oil, peanut oil, sesame oil, ethyl oleate, isopropyl myristate, and benzyl benzoate.

2.2.3 Transdermal, Topical and Mucosal Dosage Forms

Transdermal, topical, and mucosal dosage forms include, but are not limited to, ophthalmic solutions, sprays, aerosols, creams, lotions, ointments, gels, solutions, emulsions, suspensions, or other forms known to one of skill in the art. Transdermal dosage forms include "reservoir type" or "matrix type" patches, which can be applied to the skin and worn for a specific period of time to permit the penetration of a desired amount of active ingredients.

Suitable carriers and other materials that can be used to provide transdermal, topical, and mucosal dosage forms are well known to those skilled in the pharmaceutical arts, and depend on the particular tissue to which a given pharmaceutical composition or dosage form will be applied.

Depending on the specific tissue to be treated, additional components may be used prior to, in conjunction with, or subsequent to treatment with active ingredients of the invention. For example, penetration enhancers may be used to assist in delivering active ingredients to the tissue.

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates may also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition 2.3 Method of Use The present disclosure also encompasses a method for the treatment and/or prophylaxis of a subject having a malignant neoplasm. The method comprises administering to the subject a therapeutically or prophylactically effective amount of the compound of formula (I) described above.

Examples of the malignant neoplasm treatable by the present method include but are not limited to, carcinoma, sarcoma, lymphoma, leukemia, germ cell tumor, blastoma, brain cancer, medulloblastoma, glioma, head and neck cancer, oral cancer, laryngeal cancer, nasopharynx cancer, thyroid cancer, myeloid neoplasm, lung cancer, non-small cell lung cancer, small cell lung cancer, mesothelioma, hepatocellular carcinoma, lymphoid neoplasm, bone cancer, Ewing sarcoma, osteosarcoma, skeletal cancer, muscle cancer, rhabdomyosarcoma, skin cancer, basal cell carcinoma, squamous cell carcinoma, connective tissue cancer, fibrosarcoma, cartilage cancer, chondrosarcoma, nerve tissue cancer, neuroblastoma, gastric cancer, esophageal cancer, pancreatic cancer, kidney cancer, bladder cancer, prostate cancer, breast cancer, triple-negative breast cancer, testicular cancer, ovarian cancer, uterine cancer, fallopian tube cancer, and cervical cancer.

According to some embodiments of the present disclosure, the subject has the breast cancer.

Alternatively or in addition, the present method further includes the step of determining whether the breast cancer of the subject is a triple-negative breast cancer (TNBC) prior to, during or post the administration of the present pharmaceutical composition to the subject. Whether the breast cancer is the TNBC may be determined by measuring the expression of ER, PR and/or HER-2 in the breast cancer cells. In some embodiments, the TNBC are further investigated for the expression of aldehyde dehydrogenase (ALDH) or other marker (e.g., CD44, CD24 and etc). Cancer cells that are positive for functional ALDH are considered as highly tumorigenic. The expression of cell surface receptors or markers (e.g., ER, PR, HER-2, CD44, CD24, and etc) may be determined by any method known in the related art, such as genotyping and anti-receptor antibody. As to ALDH, it may be determined by methods known in the art, such as by ascertaining the cellular conversion of BODIPY-acetaldehyde (BAAA) into a fluorescent molecule BODIPYaminoacetate (BAA).

According to some embodiments of the present disclosure, the breast cancer (e.g., TNBC) is resistant to conventional chemotherapy, which may be a hormone-based chemotherapeutic agent, an antibody-based chemotherapeutic agent, or a platinum-based chemotherapeutic agent. Examples of platinum-based chemotherapeutic agent include, but are not limited to, cisplatin, oxaliplatin, carboplatin and the like. Examples of antibody-based chemotherapeutic agent include, but are not limited to, trastuzumab, pertuzumab, bevacizumab, and the like. Examples of hormone-based chemotherapeutic agent include, but are not limited to, tamoxifen, raloxifene, fulvestrant, toremifene, aromatase inhibitor (e.g., anastrozole, exemestane, letrozole, and etc), and the like.

According to further embodiments of the present disclosure, the malignant neoplasm has been metastatic, in which the cancer cells have spread to one or more parts of the body.

Advantageously, the compound of formula (I) is administered in an amount of 0.001 mg to 500 mg per day, such as 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500 mg per day. More preferably, the compound of formula (I) is administered in an amount of 0.01 mg to 250 mg per day, such as 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250 mg per day. Most preferably, the compound of formula (I) is administered in an amount of 0.1 mg to 100 mg per day, such as 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 mg per day.

Alternatively, the compound of formula (I) may be administered up to about 500 mg/m$^2$, such as 1.0, 2.0, 3.0, 4.0, 5.0, 6.0, 7.0, 8.0, 9.0, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500 mg per square meter.

The compound of formula (I) may be administered one or more times per day, such as twice, or thrice per day, by dividing the daily dose mentioned above for two- or three-times administration. For example, a daily dose of 500 mg will be administered in a proportion of two doses of 250 mg each. It is understood that each dose may consist of one or more pharmaceutical forms, for example, a dose of 250 mg may consist of two pharmaceutical forms of 125 mg each.

Alternatively, the compound of formula (I) may be formulated into sustained release form and administered one or more times per week or month, e.g., once, twice or thrice per week or month.

The amount, route of administration and dosing schedule of the compound of formula (I) will depend upon factors such as the specific indication to be treated, prevented, or managed, and the age, sex and condition of the patient. The roles played by such factors are well known in the art, and may be accommodated by routine experimentation. The compound of formula (I) of the present disclosure may be administered to the subject via intravascular delivery (e.g., injection or infusion), oral, enteral, rectal, pulmonary (e.g., inhalation), nasal, topical (including transdermal, buccal and sublingual), intravesical, intravitreal, subconjunctival, intraperitoneal, vaginal, brain delivery (e.g., intra-cerebroventricular, and intracerebral), CNS delivery (e.g., intrathecal, perispinal, and intra-spinal) or parenteral (e.g., subcutaneous, intramuscular, intravenous, and intradermal), transmucosal administration or administration via an implant, or other delivery routes known in the art.

The present invention will now be described more specifically with reference to the following embodiments, which are provided for the purpose of demonstration rather than limitation. While they are typically of those that might be used, other procedures, methodologies, or techniques known to those skilled in the art may alternatively be used.

EXAMPLES

Materials and Methods

Cell Culture

Each type of cells used in the present study were grown in manufactures' suggested medium supplemented with 10% heat-inactivated fetal bovine serum, 100 units/mL penicillin, and 100 µg/mL streptomycin, at 37° C. in a humidified 5% $CO_2$ incubator.

Anti-Proliferative Activity Assay

Cells were seeded in 96-well plates and maintained for 14-16 hours, then were treated with dimethylsulfoxide (DMSO) or test compound at various concentrations (i.e., 0.312, 1.25, 5, 20 µM) for 72 hrs. The cells were then washed with phosphate buffer saline (PBS) twice, added a medium containing 3-(4,5-dimethylthiazol-2-yl)-2,5-diphenyltetrazolium bromide (MTT) at a final concentration of 0.5 mg/mL, and incubated for 4 hr at 37° C. in a humidified incubator containing 5% $CO_2$ in air. Cells having functional succinate dehydrogenase of mitochondria would convert MTT to formazan. Then, the medium was replaced with 100 µL of DMSO for 30 min at room temperature, and the 96-well plate was read by an ELISA reader at 550 nm to get the absorbance density values. The $IC_{50}$ values of death cell lines were calculated accordingly.

Mammosphere Formation Assay

Since the breast cancer stem cells formed a mass of colonies in the form of floating spheres without attaching to a surface of a plate, the size and number of the masses were observed by a mammosphere formation assay to determine a cancer-stem-cell-specific effect.

Single-cell suspension was cultured at a density of 1,000 to 15,000 cells/well using a MammoCult™ Human Medium kit (Stemcell Technologies Inc Vancouver, CA), and the spherical cells were counted and observed under a microscope.

ALDEFLUOR Assay

The cells were stained with 1.5 mM bodipy-aminoacetaldehyde (BAAA), and then cultured at 37° C. for 45 minutes. An ALDH1 inhibitor, diethyl aminobenzaldehyde (DEAB), was used as the negative control. The stained cells were assayed using BD FACS Aria III. In this case, the positive fluorescent ALDH1-expressed cells (ALDH+) were detected in a green fluorescent channel (520 to 540 nm).

Xenograft Animal Model of Liver Cancer or Breast Cancer

Hepatocellular carcinoma LM3 cells ($5 \times 10^4$ cells/20 µL) or breast cancer MDM-BA-231 cells ($5 \times 10^4$ cells/20 µL) were implanted subcutaneously in the flanks of athymic NCr nude mice. A total of 40 male NCr nude mice (8 weeks or older weighing 20-24 g or more) were used for the tumor xenografts. The tested compounds (e.g., $Ru^{TEN}$ 1, $Ru^{TEN}$ 3, or salinomycin) were intraperitoneally administered at the dose of 10 or 20 µM/Kg twice per week. Tumor volume was determined by image analysis. The mice in the control group received corresponding injection of 0.1% DMSO. For tumor-bearing NCr nude mice during the 4-weeks (or 28 days) experiment, the % body weight changes refer to: (the total weight on reading day/the total weight on day treatment started)×100. All mice were sacrificed at the end of the experiment (i.e., by the end of 28 days), and tissues including lung, liver, tumor, heart, brain, kidneys, spleen and colon were harvested, and checked for any sign of cancer metastasis.

Example 1: Synthesis of the Present $Ru^{TEN}$ 1, $Ru^{TEN}$ 2, $Ru^{TEN}$ 3, and $Ru^{TEN}$ 4 Complexes $Ru^{TEN}$1: [(η6-1,3,5-triisopropybenzene)RuCl(4-methoxy-N-(2-quinolinyl-methylene)-aniline)]Cl

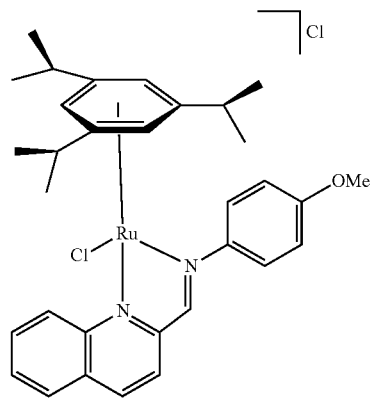

2-Quinolinecarboxaldehyde (157 mg, 1 mmol) and p-anisidine (123 mg, 1 mmol) were added to a minimal amount of dry EtOH (5 mL) and stirred at room temperature for 72 h. The solvent was removed in vacuo and dried. The resulting crude yellowish brown solid L3 was used for the next step without any further purification.

$^1$H NMR (500 MHz, CDCl3): δ 8.82 (s, 1H, PhN═CH), 8.37 (d, 3JHH=8 Hz, 1H, quinolinyl), 8.24 (d, 3JHH=8 Hz, 1H, quinolinyl), 8.16 (d, 3JHH=9 Hz, 1H, quinolinyl), 7.87 (d, 3JHH=8 Hz, 1H, quinolinyl), 7.76 (t, 3JHH=7 Hz, 1H, quinolinyl), 7.60 (t, 3JHH=7 Hz, 1H, quinolinyl), 7.41 (d, 3JHH=9 Hz, 2H, CH4OMe), 6.98 (d, 3JHH=9 Hz, 2H, CH4OMe) ppm.

[(η6-1,3,5-Triisopropylbenzene)RuCl$_2$]$_2$ (244 mg, 0.324 mmol) and crude L3 (167 mg, 0.648 mmol) were added to MeOH (40 mL) and stirred at rt for 12 hrs. The solvent was removed in vacuo and reconstituted in a minimum amount of MeOH (2 mL). Diethyl ether (40 mL) was then added to precipitate the product. The suspension was filtered and the resulting solid washed with ether (3×10 mL). The final product was then dried in vacuo for 1 hr to give a reddish brown solid. Yield: 290 mg (71%).

$^1$H NMR (400 MHz, DMSO): δ 9.09 (s, 1H, PhN═CH), 8.96 (d, 3JHH=9 Hz, 1H, quinolinyl), 8.85 (d, 3JHH=8 Hz, 1H, quinolinyl), 8.25 (d, 3JHH=8 Hz, 2H, quinolinyl), 8.12 (m, 1H, quinolinyl), 8.11 (d, 3JHH=9 Hz, 2H, CH4OMe), 7.97 (t, 3JHH=8 Hz, 1H, quinolinyl), 7.19 (d, 3JHH=9 Hz, 2H, CH4OMe), 5.54 (s, 3H, C$_6$H$_3$), 3.90 (s, 3H, C$_5$H$_3$), 2.44 (sept, 3JHH=7 Hz, 3H, CHMe$_2$), 1.16 (d, 3JHH=7 Hz, 9H, C(CH$_3$)$_2$), 0.85 (d, 3JHH=7 Hz, 9H, C(CH$_3$)$_2$) ppm. ESI-MS: (+ mode) m/z=603 [M]+. Purity of the complex was determined to be >95% pure by elemental analysis. Anal. Calcd for RuC$_{32}$H$_{38}$N$_2$Cl$_2$O (%): C 60.16, H 6.00, N 4.39. Found: C 60.26, H 5.61, N 4.45.

Ru^TEN2: [(η6-hexamethylbenzene)RuCl(4-methoxy-N-(2-quinolinyl-methylene)-aniline)]Cl

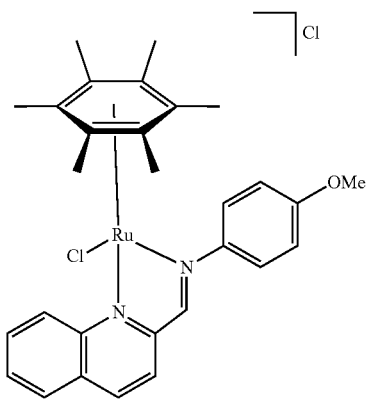

2-quinolinecarboxaldehyde (78.5 mg, 0.5 mmol) and p-anisidine (61.5 mg, 0.5 mmol) was added to minimal amount of dry EtOH (5 mL) and stirred at room temp. for 72 h. The solvent was removed in vacuo. The resulting crude yellowish brown solid [4-methoxy-N-(2-quinolinylmethylene)-aniline] was used for the next step without any further purification. [(η6-hexamethylbenzene)RuCl$_2$]$_2$ (167. mg, 0.25 mmol) was then added to the crude 4-methoxy-N-(2-quinolinylmethylene)-aniline (131 mg, approx. 0.50 mmol) and stirred in MeOH (15 mL) for 12 hrs. The solvent was removed in vacuo and the resulting crude product was purified by silica gel column chromatography (Gradient elution: 1:4 v/v EtOH/CHCl3, Rf=0.4; 1:1 v/v EtOH/CHCl3, Rf=0.7). The final product was then dried in vacuo for 1 h to give a deep red solid. Yield: 110 mg (37%).

$^1$H NMR (400 MHz, DMSO-d6): δ 8.99 (s, 1H), 8.83 (d, J=8 Hz, 1H), 8.37 (d, J=9 Hz, 1H), 8.28 (t, J=8 Hz, 2H), 8.15 (t, J=9 Hz,1H), 7.96 (m, 3H), 7.22 (d, J=9 Hz, 2H), 3.88 (s, 3H), 1.75 (s, 18H) ppm. ESI-MS (+ve mode): m/z=561 [M]+. Analysis (Calcd., found for C$_{29}$H$_{32}$N$_2$Cl$_2$ORu.0.5H$_2$O): C (57.52, 57.55), H (5.49, 5.23) N (4.63, 4.58). RP-HPLC (% Purity): 98.1% at 214 nm and 98.6% at 254 nm; tr=19.8 min.

Ru^TEN3: [(η6-1,3,5-triisopropybenzene)RuCl(3-chloro-N-(2-quinolinylmethylene)-aniline)]Cl

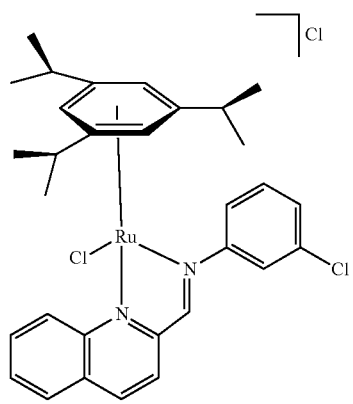

2-Quinolinecarboxaldehyde (78.6 mg, 0.5 mmol) and 3-chloroaniline (52.9 mg, 0.5 mmol) was added to dry EtOH (10 mL) and stirred at r.t. over 24 h. The solvent was removed in vacuo and dried. The resultant crude 3-chloro-N-(2-quinolinylmethylene)aniline (133 mg, approx. 0.5 mmol) was treated with [(η6-1,3,5-triisopropylbenzene)RuCl$_2$]$_2$ (188 mg, 0.25 mmol) in MeOH (20 mL) and stirred at room temp. over 12 h. The solvent was removed in vacuo and the resulting solid purified by column chromatography (1:4 v/v EtOH/CHCl$_3$, Rf=0.6). The purified product was redissolved in CHCl3 and filtered through a syringe column to remove trace amount of dissolved silica, before the solvent was removed in vacuo. The final product was then dried in vacuo for 1 hr to give a dark red solid. Yield: 89 mg (28%).

$^1$H NMR (400 MHz, MeOD-d4): δ 9.02 (d, 3JHH=9 Hz, 1H, quinolinyl), 9.00 (s, 1H, PhN=CH), 8.79 (d, 3JHH=8 Hz, 1H, quinolinyl), 8.25 (m, 3H, quinolinyl/C6H4), 8.15 (t, 3JHH=8 Hz,1H, quinolinyl/C$_6$H$_4$), 8.06 (dt, 3JHH=5 Hz, 1H, quinolinyl/C$_6$H$_4$), 7.99 (t, 3JHH=8 Hz,1H, quinolinyl/C6H4), 7.65 (d, 3JHH=5 Hz, 2H, quinolinyl/C$_6$H$_4$), 5.60 (s, 3H, C$_6$H$_3$), 2.49 (sept, 3JHH=7 Hz, 3H, CHMe$_2$), 1.23 (d, 3JHH=7 Hz, 9H, CH(CH$_3$)$_2$), 0.97 (d, 3JHH=7 Hz, 9H, CH(CH$_3$)$_2$) ppm. ESI-MS (+ve mode): m/z=607 [M]+.

Purity of the complex was determined to be >95% pure by elemental analysis. Anal. Calcd for C$_{31}$H$_{35}$Cl$_3$N$_2$Ru.3H$_2$O (%): C 53.41, H 5.93, N 4.02; Found: C 53.02, H 5.66, N 3.87.

Ru^TEN4: [(η6-Hexamethylbenzene)RuCl(3-chloro-N-(2-quinolinylmethylene)aniline)]Cl

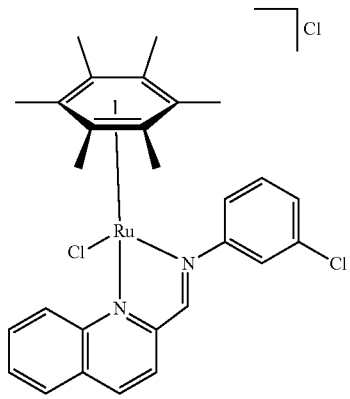

2-Quinolinecarboxaldehyde (78.6 mg, 0.5 mmol) and 3-chloroaniline (52.9 μL, 0.5 mmol) were added to dry EtOH (8 mL) and stirred at rt over 72 h. The solvent was removed in vacuo and dried. Crude 3-chloro-N-(2-quinolinylmethylene)aniline (135 mg) was treated with [(η6-hexamethylbenzene)RuCl$_2$]$_2$ (167 mg, 0.25 mmol) in MeOH (20 mL) and stirred at room temp for over 12 h. The solvent was removed in vacuo and the resulting solid purified by gradient elution column chromatography (1:4 v/v EtOH/CHCl$_3$, Rf=0.2; 1:1 v/v EtOH/CHCl$_3$, Rf=0.6). The final product was then dried in vacuo for 1 h to give a red solid. Yield: 182 mg (61%).

$^1$H NMR (400 MHz, CDCl$_3$): δ 9.37 (s, 1H, PhN=CH), 8.68 (d, 3J=8 Hz, 1H, quinolinyl), 8.52 (d, 3JHH=9 Hz, 1H, quinolinyl), 8.48 (d, 3JHH=8 Hz, 1H, quinolinyl), 8.40 (d, 3JHH=8 Hz, 1H, quinolinyl), 8.34 (s, 1H, C6H4), 7.99 (d, 3JHH=8 Hz, 1H, C6H4), 7.88 (t, 3JHH=7 Hz, 1H, quinolinyl), 7.79 (t, 3JHH=7 Hz, 1H, quinolinyl), 7.54 (t, 3JHH=8 Hz, 1H, C6H4), 7.44 (d, 3JHH=8 Hz, 1H, C6H4), 1.90 (s, 18H, C6(CH3)6) ppm. ESI-MS: (+mode) m/z=565 [M]+. Purity (HPLC): 97.4% at 214 nm and 95.6% at 254 nm; tR=20.3 min. Purity of the complex was determined to be >95% pure by HPLC.

Alternative synthetic Route for Ru$^{TEN}$3 and Ru$^{TEN}$4

2-Quinolinecarboxaldehyde (314 mg, 2 mmol) and 3-chloroaniline (268 mg, 4 mmol) were placed to a 50 mL round-bottom flask equipped with a Dean-Stark apparatus. 25 mL of toluene was added to dissolve the reactants and the resulting brown solution was refluxed overnight. The mixture was allowed to cool and concentrated under reduced pressure to give the dark brown oil which was dissolved in a minimal amount of diethyl ether. The black insoluble residue was filtered and the solution was again concentrated under reduced pressure and dried in vacuo to give a brown semi-solid. The crude product containing small amount of unreacted 3-chloroaniline was used without additional purification.

$^1$H NMR (300 MHz, d6-DMSO): δ 8.79 (s, 1H, Ph-N=CH), 8.53 (d, J=8.6 Hz, 1H, quinolinyl), 8.29 (d, J=8.6 Hz, 1H, quinolinyl), 8.12 (dd, J=15.9, 7.9 Hz, 2H, quinolinyl), 7.90-7.83 (m,1H, quinolinyl), 7.76-7.69 (m, 1H, quinolinyl), 7.54-7.47 (m, 2H, quinolinyl), 7.43-7.35 (m, 2H, quinolinyl).

The corresponding [(η6-arene)RuCl$_2$]$_2$ (0.15 mmol) and 3-chloro-N-(2-quinolinylmethylene)-aniline (180 mg, 0.675 mmol) were dissolved in 10 mL of dry MeOH under N$_2$ atmosphere and stirred for 48 h. A resulting brown solution was evaporated under reduced pressure and the brown residue was washed with copious amounts of diethyl ether. The solid was subsequently dissolved in minimal amount of CH$_2$Cl$_2$ and eluted through a short layer of neutral Al$_2$O$_3$ (5 cm) by CH$_2$Cl$_2$ to remove unreacted 3-chloro-N-(2-quinolinylmethylene)aniline and 3-chloroaniline. The product was eluted with CHCl$_3$/MeOH mixture (9:1) and the red filtrate was evaporated to dryness under reduced pressure. The red solid was redissolved in a minimal amount of dichloromethane and centrifuged (13,000 rpm for 7 min) to remove the undissolved residues. The red microcrystals of Ru$^{TEN}$3 or needle-shaped X-ray quality single crystals of Ru$^{TEN}$4 were produced by slow diffusion of diethyl ether into the CH$_2$Cl$_2$ solution. Crystals were washed with diethyl ether and dried in vacuo.

Complex Ru$^{TEN}$3. Yield: 38 mg (20%). Anal. Calcd, C$_{31}$H$_{35}$Cl$_3$N$_2$Ru.0.25 CH$_2$Cl$_2$ (%): C, 56.50; H, 5.39; N, 3.22. Found: C, 56.09; H, 5.04; N, 4.46.

Complex Ru$^{TEN}$4. Yield: 40 mg (22%). Anal. Calcd, C$_{28}$H$_{29}$Cl$_3$N$_2$Ru.2CH$_2$Cl$_2$.0.25 H$_2$O (%): C, 50.45, H, 4.60, N, 4.06. Found: C, 50.36, H, 5.01, N, 4.21.

Example 2: Synthesis and Characterization of Additional Ru$^{TEN}$ Complexes

In this example, 40 Ru$^{TEN}$ complexes (i.e., compounds 1 to 40) were synthesized in accordance with the procedures described in scheme 1. Each Ru$^{TEN}$ complex was then investigated for its ability in reducing the viability of mammospheres by means of an Alamar Blue assay, and results are summarized in Table 1 and FIG. 1, in which FIG. 1 depicts representative dose-response curves of compounds 1 to 3 in suppressing the growth of MDA-MB-231 mammospheres.

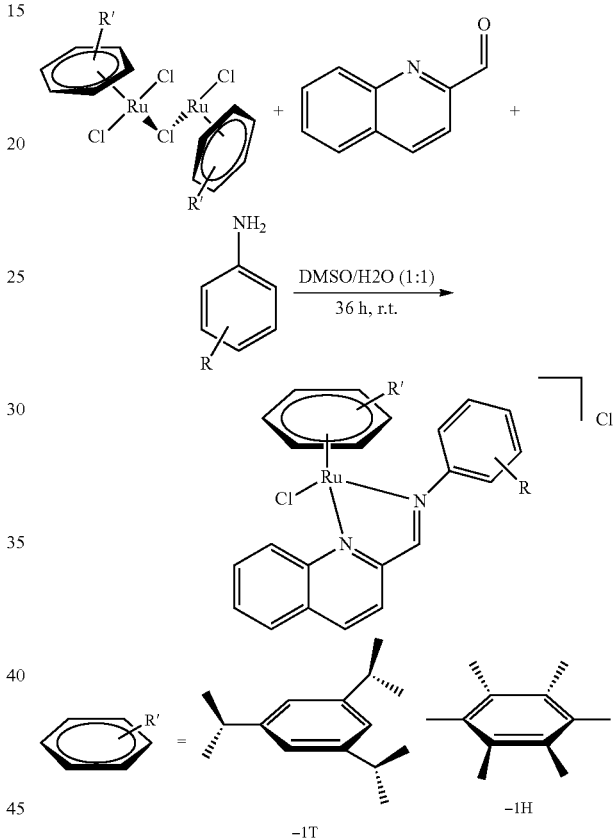

Scheme 1.

TABLE 1

Effects of RU$^{TEN}$ complexes on growth of MDA-MB-231 mammospheres using Alamar Blue assay

| Compd # | IC$_{50}$ (μM) -1T | R | IC$_{50}$ (μM) -1H | Compd # |
|---|---|---|---|---|
| 1 | 0.618 | | >20 | 21 |

TABLE 1-continued

Effects of RU$^{TEN}$ complexes on growth of MDA-MB-231 mammospheres using Alamar Blue assay

| Compd # | IC$_{50}$ (μM) −1T | R | IC$_{50}$ (μM) −1H | Compd # |
|---|---|---|---|---|
| 2 | 1.475 | 4-isopropylphenyl | ND | 22 |
| 3 | 0.583 | 4-(dimethylamino)phenyl | ND | 23 |
| 4 | 2.6 | phenyl | >20 | 24 |
| 5 | >20 | 4-methylphenyl | 11 | 25 |
| 6 | 3.6 | 3-methoxyphenyl | 19 | 26 |
| 7 | 14 | 4-hydroxyphenyl | >20 | 27 |
| 8 | >20 | 3-hydroxyphenyl | >20 | 28 |
| 9 | 3.5 | 4-chlorophenyl | >20 | 29 |
| 10 | >20 | 3-bromophenyl | 13 | 30 |
| 11 | 3.9 | 3-trifluoromethylphenyl | 14 | 31 |

TABLE 1-continued

Effects of RU$^{TEN}$ complexes on growth of MDA-MB-231 mammospheres using Alamar Blue assay

| Compd # | IC$_{50}$ (μM) −1T | R group | IC$_{50}$ (μM) −1H | Compd # |
|---|---|---|---|---|
| 12 | >20 | 4-SO$_2$H phenyl | >20 | 32 |
| 13 | >20 | 3-SO$_2$NH$_2$ phenyl | >20 | 33 |
| 14 | >20 | 2-SO$_2$NH$_2$ phenyl | >20 | 34 |
| 15 | >20 | 4-CONH$_2$ phenyl | >20 | 35 |
| 16 | >20 | 3-CONH$_2$ phenyl | >20 | 36 |
| 17 | >20 | 3-amidino phenyl (HN=C(NH$_2$)-) | >20 | 37 |
| 18 | 16 | 1-naphthyl | 8.9 | 38 |
| 19 | 9.5 | 2-naphthyl | 13 | 39 |

TABLE 1-continued

Effects of RU$^{TEN}$ complexes on growth of MDA-MB-231 mammospheres using Alamar Blue assay

| Compd # | -1T IC$_{50}$ (μM) | R | -1H IC$_{50}$ (μM) | Compd # |
|---|---|---|---|---|
| 20 | >20 | (phenyl-R) | >20 | 40 |
| Ru$^{TEN}$1 | 2.2 | (1-hydroxynaphthyl) | | |
| | | (4-OMe phenyl) | >20 | Ru$^{TEN}$2 |
| Ru$^{TEN}$3 | 2.7 | (3-Cl phenyl) | 11 | Ru$^{TEN}$4 |

ND: Not determined.

Example 3: Characterization of the Ru$^{TEN}$ Complexes of Example 1

3.1 Cytotoxicity

The Ru$^{TEN}$ complexes of Example 1 were evaluated for their anti-proliferative properties in two breast cancer cell lines, namely, MCF-7 and MDA-MB-231 cells via MTT assay. MCF-7 and MDA-MB-231 breast cancer cell lines significantly differ from each other by their sensitivity to traditional chemotherapeutic drugs. MCF-7 is a chemotherapy-responsive breast cancer cell line of luminal subtype with high expression of estrogen receptor (ER), whereas MDA-MB-231 is a triple negative breast cancer (TNBC) or basal-like breast cancer cell ine. TNBC is defined as highly invasive cancer that lacks expression of ER, progesterone receptor (PR) and Her-2; it has one of the worst outcomes among all subtypes of breast cancers. The aggressive nature of TNBC may be related to the presence of breast cancer stem cells within the tumor; therefore, MDA-MB-231 cells are often used as a model of mammary cancer stem cells.

The cytotoxicity of Ru$^{TEN}$ complexes of Example 1 was compared to that of cisplatin or oxaliplatin, which were known to induce their anticancer effects by the mode of action different from ER stress. Three CSC-selective organic compounds, salinomycin, etoposide and abamectin, were also used for comparison. Briefly, MCF-7 and MDA-MB-231 cells were respectively treated with increasing concentrations of compounds of interest for 24 or 72 hrs and then the cell viability was measured. Results are summarized in Table 2.

TABLE 2

Cytotoxicity of Ru$^{TEN}$ complexes

| | IC$_{50}$ (μM) | | | |
|---|---|---|---|---|
| Name of Compound | MCF-7 72 h | MDA-MB-231 24 h | MDA-MB-231 72 h | MDA-MB-231 mammospheres 72 h |
| Ru$^{TEN}$1 | 0.68 ± 0.23 | 1.2 ± 0.1 | 0.28 ± 0.1 | 1.4 ± 0.1 |
| Ru$^{TEN}$2 | 4.1 ± 0.9 | 10 ± 1 | 2.2 ± 0.3 | >40 |
| Ru$^{TEN}$3 | 4.4 ± 0.4 | 4.5 ± 0.8 | 1.5 ± 0.3 | 1.7 ± 0.3 |
| Ru$^{TEN}$4 | 2.5 ± 0.7 | 9.2 ± 1.3 | 1.4 ± 0.3 | 7.2 ± 1.8 |
| Cisplatin | 22 ± 7 | 268 ± 78 | 27 ± 8 | >40 |
| Oxaliplatin | 1.1 ± 0.2 | 348 ± 78 | 4.6 ± 1.0 | >40 |
| Saliomycin | 0.51 ± 0.03 | 31 ± 4 | 0.56 ± 0.09 | 8.3 ± 2.4 |
| Etoposide | 0.79 ± 0.21 | >1000 | 6.4 ± 1.2 | >40 |
| Abamectin | 7.0 ± 2.2 | 18 ± 6 | 6.4 ± 2.3 | 4.0 ± 0.5 |

In general, all Ru$^{TEN}$ complexes demonstrated marked antiproliferative activity in both breast cancer cell lines in a low micromolar concentration range, whereas cisplatin was only moderately active. The cytotoxicity of Ru$^{TEN}$ complexes in resistant MDA-MB-231 cell line was 2-3 times higher than that in MCF-7.

3.2 Mammosphere Growth of Breast Cancer Stem Cells (CSCs)

Figure 2:
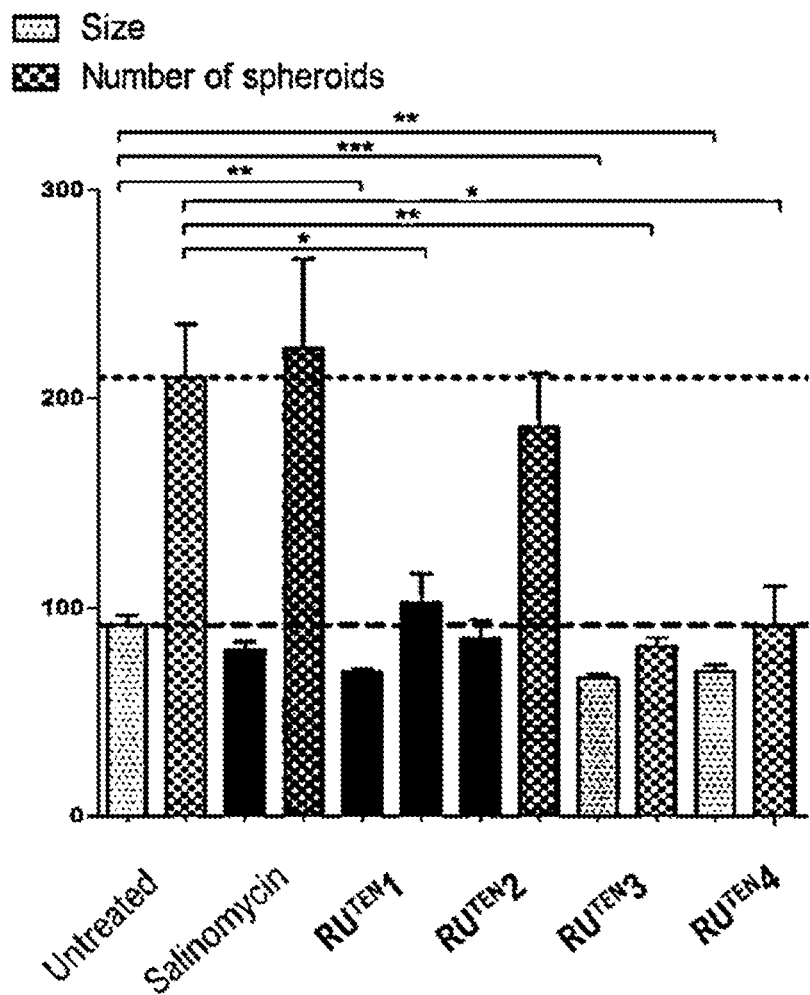
FIG. 2 is a bar graph depicting the effects of the present RU$^{TEN}$ complexes on the size and numbers of MDA-MB-231 mammospheres in accordance with one embodiment of the present disclosure.

The effects of Ru$^{TEN}$ complexes of Example 2 on breast CSCs characteristics were evaluated by mammosphere assay where cells proliferate in suspension as floating spheres. The mammosphere assay is based on the concept that when cells proliferate in three-dimensional spheroid structures, only cancer cells with stem-like characteristics are able to evade anoikis. Results are provided in Table 3 and FIG. 2.

According to Table 3, when mammo spheres were treated with salinomycin as a positive control, both size and numbers of MDA-MB-231 spheroids decreased by 30%. Similarly, the number of MCF-7 mammospheres decreased by 33%, while the size of spheroids decreased only by 9%. In contrast, CSC-selective compound etoposide did not affect the size of MDA-MB-231 and MCF-7 mammospheres and decreased their number only by 10-15%, indicating low response of mammospheres to etoposide treatment. As expected, cisplatin and oxaliplatin did not show any potency in inhibiting mammosphere growth, regardless of the cell line. In general, the effects of $Ru^{TEN}$ complexes on MDA-MB-231 mammospheres were more pronounced than on MCF-7 mammospheres, corresponding to the results obtained in monolayer cells by MTT assay. The highest potency in MDA-MB-231 was observed for $Ru^{TEN}3$ (35% decrease in number and 60% decrease in size), $Ru^{TEN}1$ (20% decrease in number and 18% decrease in size) and $Ru^{TEN}4$ (17% decrease in number and 10% decrease in size). Interestingly, $Ru^{TEN}2$ demonstrated drastically different behaviour than its structurally similar analogues and did not inhibit mammosphere growth. On the contrary to MDA-MB-231 mammo spheres, the size and number of MCF-7 mammospheres was not markedly affected by ER stress-inducing compounds with the exception of $Ru^{TEN}3$ (30% decrease in number) and $Ru^{TEN}4$ (10% decrease in number and 17% decrease in size), indicating that $Ru^{TEN}$ complexes were more effective on more tumorigenic MDA-MB-231 cells.

mammospheres, indicating attenuated self-renewal capacity of treated CSC. Next, the ability of the drugs of interest to reduce the viability of MDA-MB-231 mammo spheres by means of Alamar Blue assay was also determined, and the results were in a good agreement with the ability of $Ru^{TEN}$ complexes to affect the mammosphere growth (data not shown). Further, as expected, cisplatin and oxaliplatin did not affect the viability of MDA-MB-231 mammospheres. The cytotoxicity of $Ru^{TEN}$ complexes decreased in the following order: $Ru^{TEN}3 \approx Ru^{TEN}1 > Ru^{TEN}4 > Ru^{TEN}2$. Similar trend was observed when the effects of these compounds on the number of MDA-MB-231 mammo spheres were analyzed.

3.3 Aldehyde Dehydrogenase (ALDH) Activity

While CD44+/CD24−/low phenotype has often been associated with breast CSC/progenitor cell features, yet there is no correlation between the presence of CD44+/CD24−/low cells and clinical outcome and formation of distant metastases. It is the presence of aldehyde dehydrogenase (ALDH) bright cells which separates highly tumorigenic CD44+/CD24−/low/ALDHbright population from non-tumorigenic cells. Unlike CD44+/CD24−/low, ALDH is a predictor of metastasis and is associated with a poor clinical outcome. The main role of ALDH enzymes is the detoxification of aldehydes generated in various metabolic processes into carboxylic acids. However, several ALDH isoforms are involved in retinoic acid signaling and this particular function was linked to the "stemness" of CSCs. The functional activity of ALDHs can be accurately determined by ascertaining the cellular conversion of BODIPY-acetaldehyde (BAAA) into a fluorescent molecule BODIPY-aminoacetate (BAA). ATP-binding cassette (ABC)-

TABLE 3

Effects of $RU^{TEN}$ complexes of Example 1 on growth of mammospheres of breast cancer cells

| | Characteristics of mammospheres | | | | | |
|---|---|---|---|---|---|---|
| Name of | MCF-7 | | MDA-MB-231 | | MDA-MB-231 Secondary [a] | |
| Compound | Size (μm) | Number | Size (μm) | Number | Size (μm) | Number |
| Control | 127 ± 20 | 263 ± 77 | 117 ± 26 | 125 ± 48 | 89 ± 14 | 190 ± 72 |
| $RU^{TEN}1$ | 130 ± 15 | 238 ± 86 | 93 ± 29 | 103 ± 41 | 69 ± 3 | 102 ± 28 |
| $RU^{TEN}2$ | 114 ± 24 | 255 ± 175 | 98 ± 18 | 141 ± 41 | 85 ± 15 | 186 ± 45 |
| $RU^{TEN}3$ | 122 ± 16 | 183 ± 32 | 76 ± 19 | 50 ± 21 | 67 ± 4 | 81 ± 9 |
| $RU^{TEN}4$ | 105 ± 18 | 236 ± 88 | 95 ± 37 | 118 ± 17 | 70 ± 6 | 91 ± 33 |
| Cisplatin | 106 ± 14 | 273 ± 108 | 95 ± 25 | 136 ± 44 | 103 ± 30 | 67 ± 20 |
| Oxaliplatin | 107 ± 17 | 274 ± 93 | 99 ± 27 | 144 ± 50 | 86 ± 14 | 122 ± 10 |
| Saliomycin | 117 ± 21 | 176 ± 73 | 84 ± 25 | 87 ± 28 | 82 ± 8 | 224 ± 74 |
| Etoposide | 135 ± 6 | 237 ± 11 | 123 ± 20 | 107 ± 37 | 63 ± 4 | 73 ± 22 |
| Abamectin | 77 ± 13 | 147 ± 33 | 76 ± 8 | 4 ± 1 | N.A. | N.A. |

[a] MDA-MB-231 and MCF-7 primary mammospheres were grown in ultralow attachment conditions for 96 hr furthered incubated with compounds of interest for 72 hrs. Secondary mammospheres were grown in drug-free conditions for 7 days. The size and number of >50 μm were analyzed by ImageJ software.

Based on the findings in Table 3, the effect of $Ru^{TEN}3$ complexes on CSC self-renewal capacity was further investigated. To this purpose, drug-treated primary MDA-MB-231 mammospheres were dissociated into single cell suspensions and incubated for 7 days in ultralow attachment drug-free conditions. As can be seen from FIG. 2, single cells obtained from $Ru^{TEN}2$ or salinomycin-treated primary mammospheres could resume their growth, which was indicated by only slight changes in size and number of mammospheres in comparison with untreated mammospheres. On the other hand, cells that were obtained from primary mammospheres treated with $Ru^{TEN}1$, $Ru^{TEN}3$ and $Ru^{TEN}4$ exhibited drastically reduced propensity to form secondary transporter inhibitors in the assay buffer prevent the efflux of BAA from the cells, resulting in the accumulation of BAA in cytoplasm. In order to differentiate between the cells with high ALDH activity and cells with low or no ALDH activity, control experiments were performed in the presence of ALDH inhibitor diethylaminobenzaldehyde (DEAB).

Figure 3:
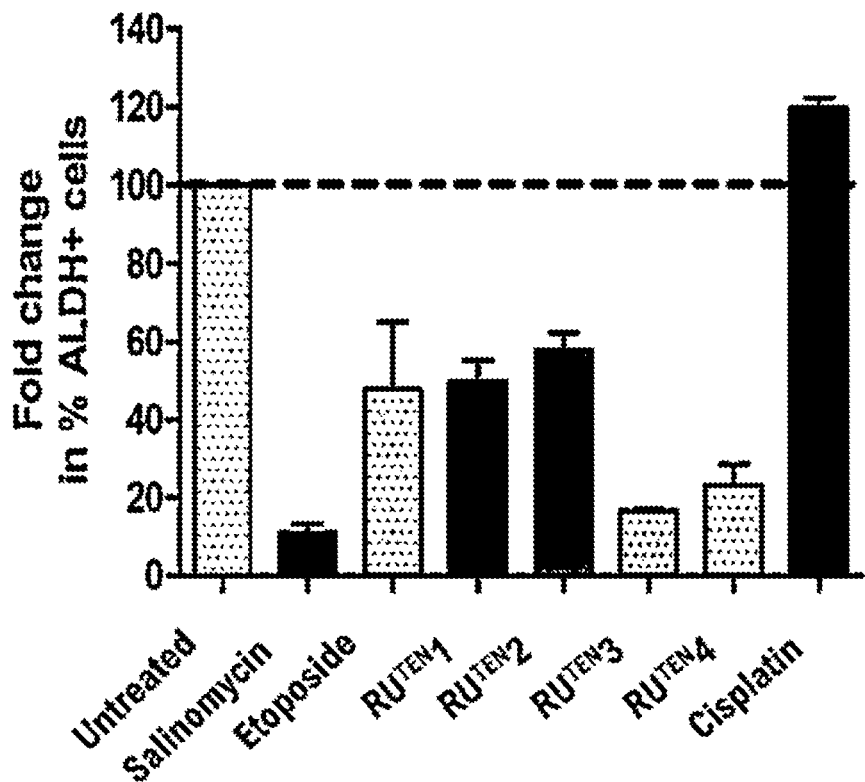
FIG. 3 illustrates the effects of the present $RU^{TEN}$ complexes on the ALDH-positive subpopulations of MDA-MB-231 cells in accordance with one embodiment of the present disclosure.

Since MDA-MB-231 consists almost exclusively of CD44+/CD24−phenotype and was shown to display higher percentage of ALDHbright subpopulation than MCF-7, the effects of the $Ru^{TEN}$ complexes on ALDH activity of MDA-MB-231 cells were investigated. The results are presented in FIG. 3.

As expected, salinomycin significantly affected the ALDHbright cells, reducing the sub-population by 89% versus control, whereas etoposide caused 52% reduction of ALDHbright sub-population. Cisplatin, however, did not affect ALDHbright cells. All ER stress-inducing $Ru^{TEN}$ complexes possessed the ability of reducing ALDHbright cell subpopulation, but to a different extent. $Ru^{TEN}1$ and $Ru^{TEN}2$ decreased ALDHbright cell subpopulation to an extend similar to that of etoposide. As for $Ru^{TEN}3$ and $Ru^{TEN}4$, both of them reduced ALDHbright cell subpopulation to a level comparable to that of salinomycin (70-80% reduction).

3.4 The Invasive Properties of MDA-MB-231 Mammospheres

CSCs are associated with highly invasive phenotype and it is believed that this subset of cancer cells gives rise to metastases. In order to monitor the dissemination of MCF-7 and MDA-MB-231 breast cancer spheroids, the spheroids were embedded into three-dimensional (3D) collagen scaffold using Aim Biotech 3D cell culture chips. Collagen with spheroids was introduced into the central region of the microfluidic system where it polymerized via thermal cross-linking. Cell culture media was introduced into media channels forcing spheroids to move through collagen towards the media.

Figure 4:
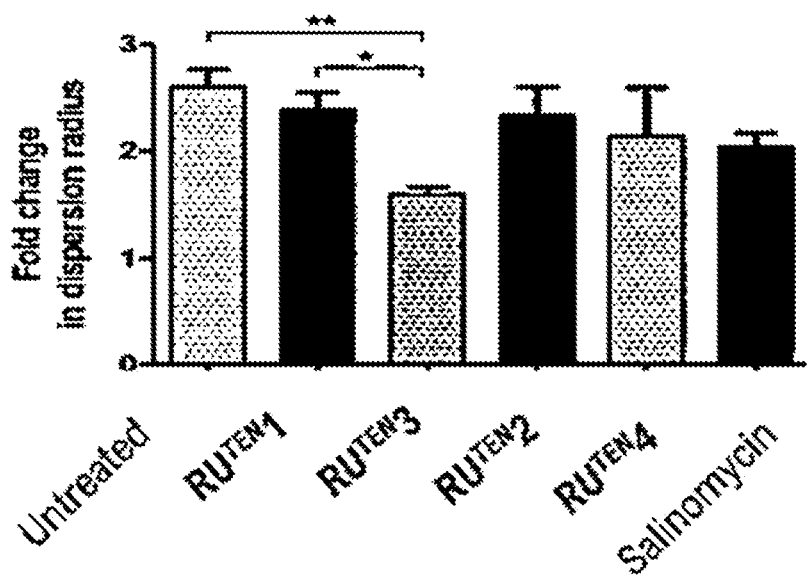
FIG. 4 illustrates the effects of the present $RU^{TEN}$ complexes on the dispersion of MDA-MB-231 cells into collagen in accordance with one embodiment of the present disclosure.
Figure 5A:
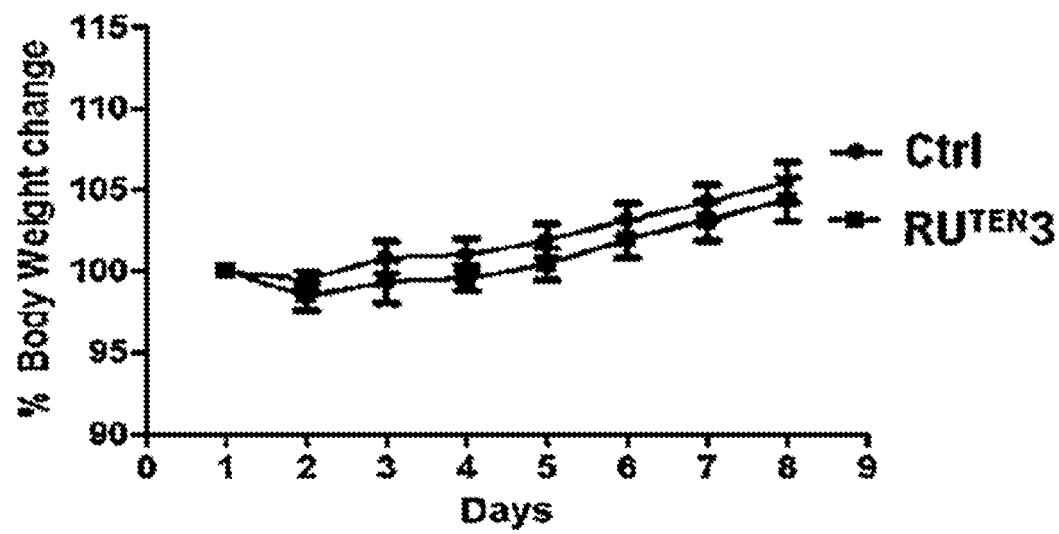
FIGS. 5(a)-5(d) depicts the effects of the present $RU^{TEN}$ complexes on the bodyweight and levels of AST, ALT and BUN in mice in accordance with one embodiment of the present disclosure.
Figure 5B:
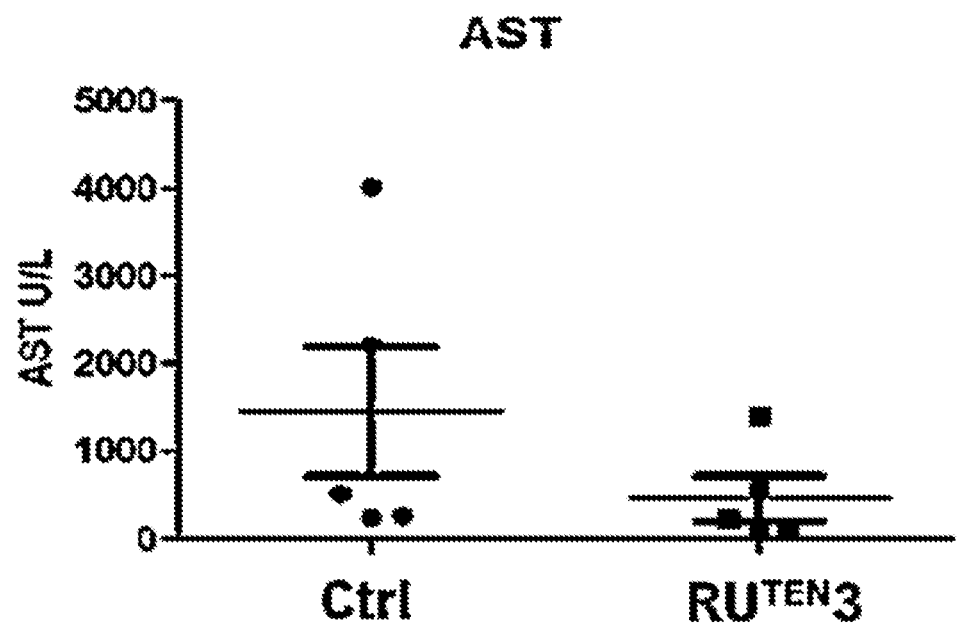
Figure 5C:
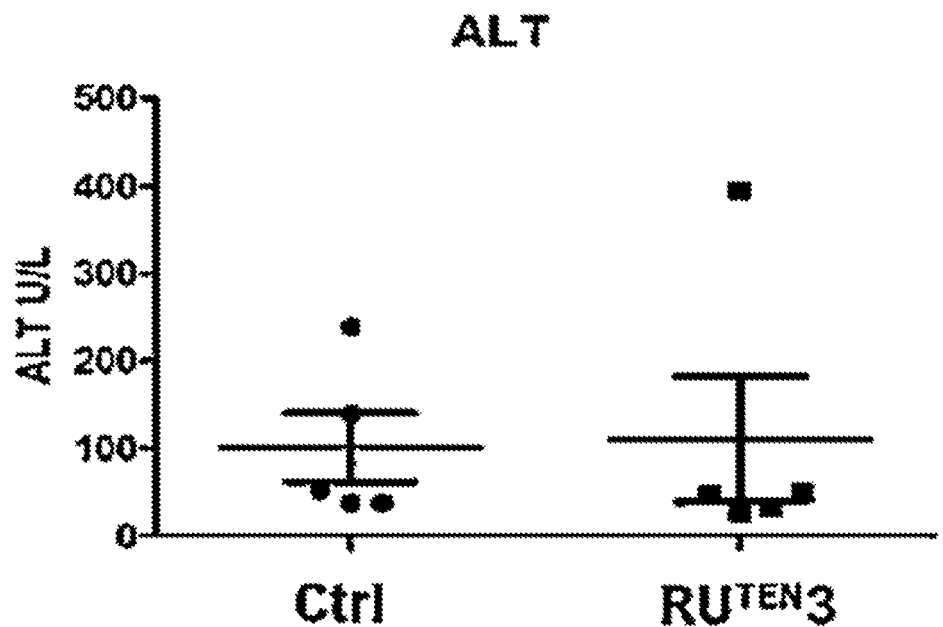
Figure 5D:
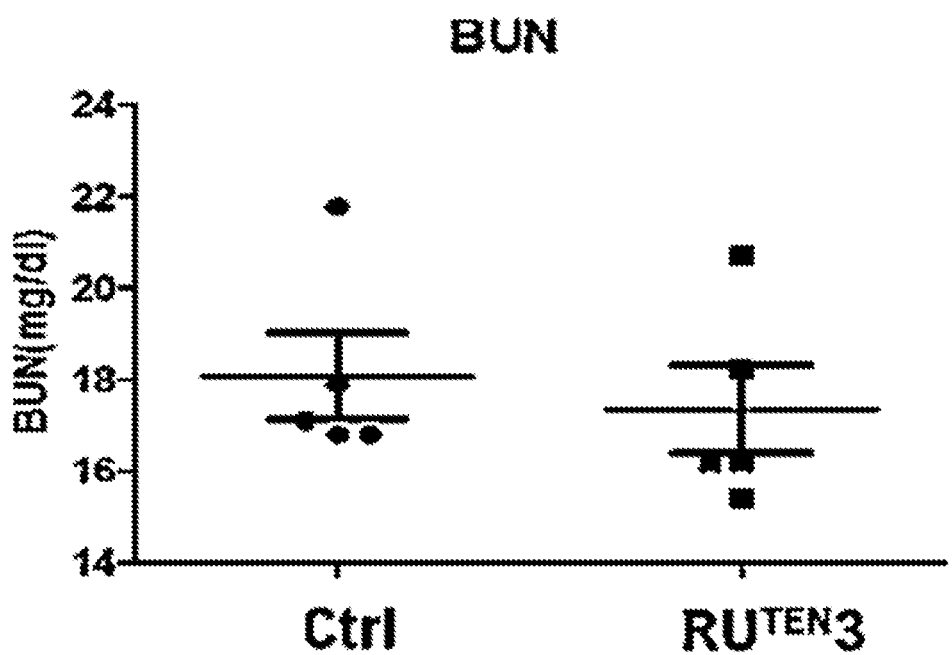

Confocal microscopy demonstrated that MCF-7 mammospheres did not dissociate within a 24 hr incubation period, whereas MDA-MB-231 mammospheres fully dissociated within the collagen (data not shown), indicating that MDA-MB-231 were highly invasive. Thus, whether $Ru^{TEN}$ complexes and salinomycin affected the invasive properties of MDA-MB-231 spheroids was then investigated. To this purpose, MDA-MB-231 monolayer cells were incubated with compounds of interest (e.g., $Ru^{TEN}$ complexes of Example1 or salinomycin) for 72 hr, then the delamination was allowed to proceed for over 28 hr. Results are depicted in FIG. 4.

When MDA-MB-231 mammospheres were treated with salinomycin, $Ru^{TEN}1$, $Ru^{TEN}2$ or $Ru^{TEN}4$, cells did not exhibit significant dispersion after 4 hr and only slight dispersion was observed after 28 hr versus untreated controls. In stark contrast, when MDA-MB-231 mammospheres were treated with $Ru^{TEN}3$, cells did not migrate from the spheroids over the entire incubation period, indicating potent anti-invasive properties of $Ru^{TEN}3$.

Example 4 In Vivo Characterization of the present $Ru^{TEN}$ Complexes

In the present example, the selected $Ru^{TEN}$ complexes were subjected to in vivo studies to evaluate their optimally tolerated doses, Ru biodistributions, and therapeutic efficacies in healthy or tumor bearing mice.

4.1 Acute Toxicity

In this example, $Ru^{TEN}3$ was subjected to in vivo studies with Balb/c mice. Various treatment regimens were explored to define the optimally tolerated dose of $Ru^{TEN}3$ in vivo. In the pilot experiment, three groups of mice were treated intraperitoneally with $Ru^{TEN}3$ from 5 to 20 µmol/kg twice a week for 33 days. The body weight changes were recorded.

Mice groups that were treated with 5 and 10 µmol/kg of $Ru^{TEN}3$, did not demonstrate any weight loss and were bright, alert and responsive during the entire treatment period, indicating low toxicity of these treatment regimens. However, when mice were treated with 20 µmol/kg of $Ru^{TEN}3$, they appeared to be experienced severe pain, stopped moving, thus were euthanized according to ethical guidelines.

In order to determine the effects of $Ru^{TEN}3$ on kidney and liver function, two groups of female NCr nude mice were treated with a single dose of 10 µmol/kg of $Ru^{TEN}3$ and a vehicle (0.1% DMSO), respectively. After 8 days of observation, the mice were euthanized and the levels of AST, ALT and BUN enzymes, indicating kidney and liver toxicity, were analyzed by use of a mice serum. The weight changes and enzyme levels are presented in FIGS. 5(a)-5(d). To conclude, we found that intraperitoneal injection of $Ru^{TEN}3$ at 10 µmol/kg did not cause any acute toxicity in NCr nude mice, characterized by death, weight loss or deviations of kidney and liver functions.

4.2 Ru Biodistribution

Figure 6:
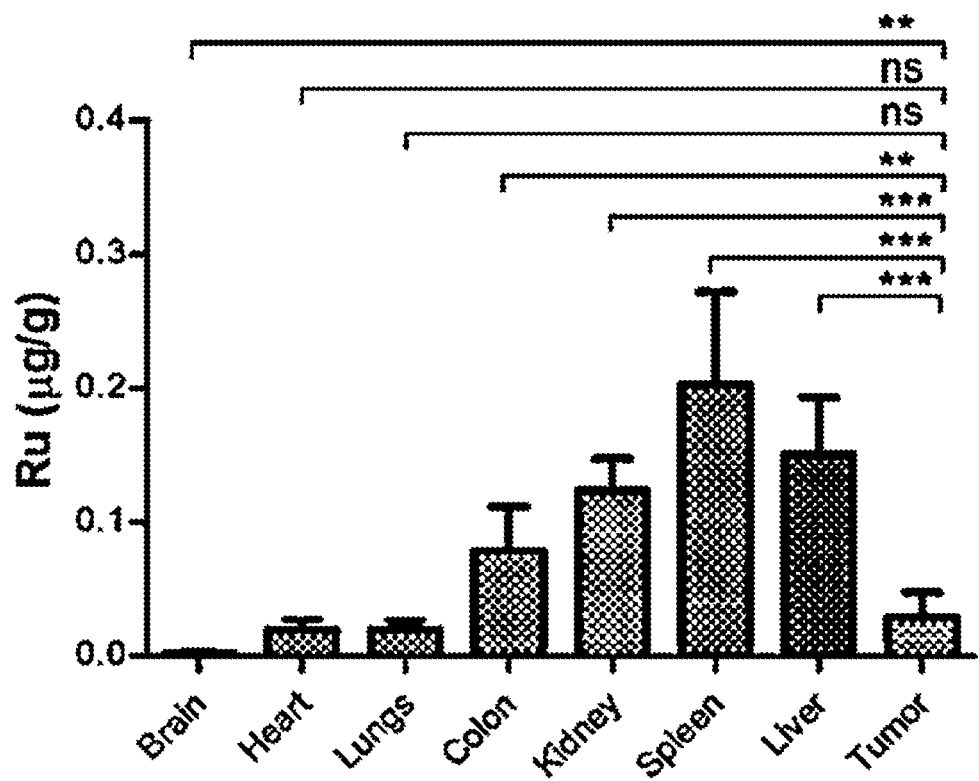
FIG. 6 depicts the accumulation of Ru in various tissues of a tumor-bearing mouse treated with the present $RU^{TEN}$ complex in accordance with one embodiment of the present disclosure.

The Ru biodistribution in tumor-bearing mice treated with $Ru^{TEN}3$ was also investigated. It was found that the highest Ru accumulation was observed in spleen and liver, followed by kidney and colon (FIG. 6). Further, it should be noted that Ru content in the brain was very low, indicating that Ru complex did not cross blood brain barrier.

4.3 $Ru^{TEN}1$ and $Ru^{TEN}3$ Effectively Suppressed Hepatocellular Carcinoma LM3 Xenografts The $Ru^{TEN}1$ and $Ru^{TEN}3$ of Example 1 were used in the present example to investigate their therapeutic efficacies on nude mice bearing human hepatocellular carcinoma LM3 xenografts.

Figure 7:
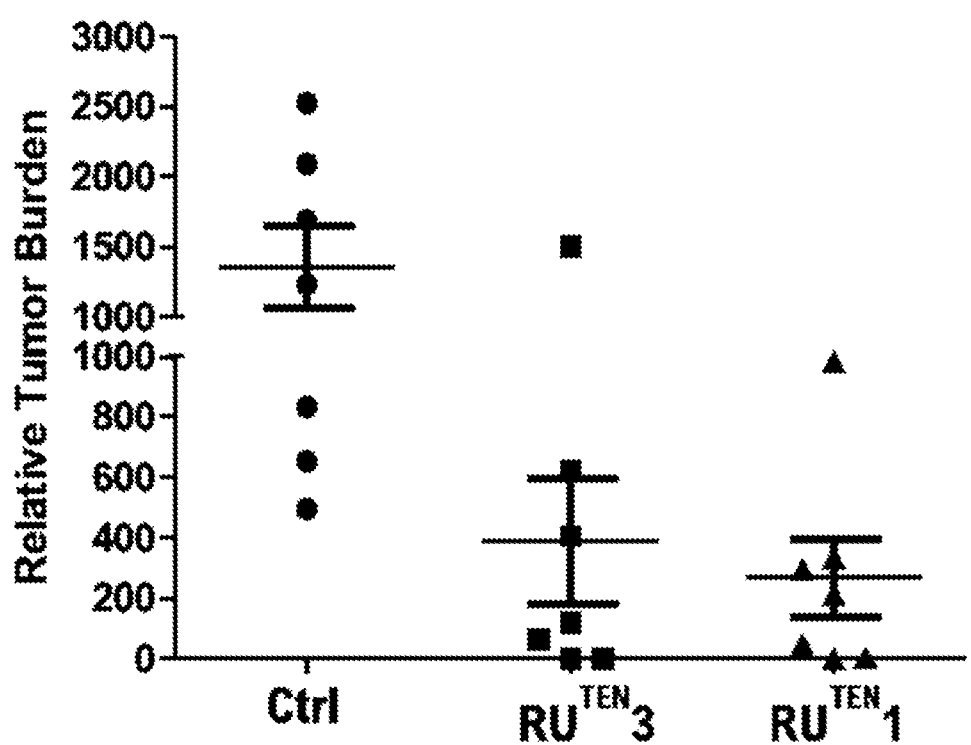
FIG. 7 depicts the effect of $Ru^{TEN}1$ and $Ru^{TEN}3$ on the tumor volume of hepatocellular carcinoma LM3 tumor-bearing mice in accordance with one embodiment of the present disclosure.
Figure 8:
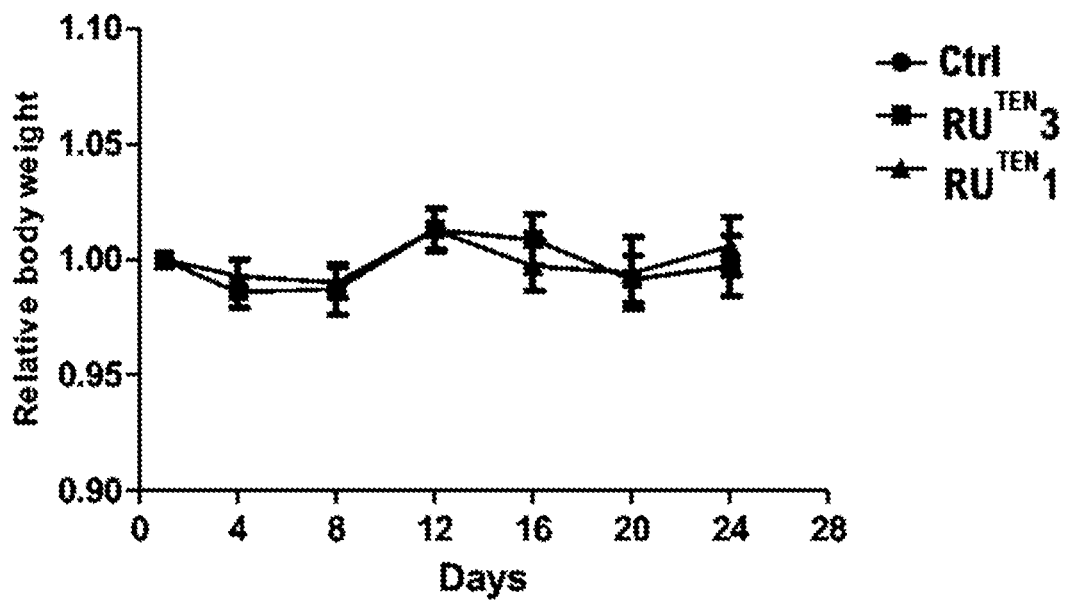
FIG. 8 depicts the effect of $Ru^{TEN}1$ or $Ru^{TEN}3$ on body weight of the hepatocellular carcinoma LM3 tumor-bearing mice of FIG. 7.

The tumor cells were subcutaneously implanted in nude mice, and the $Ru^{TEN}1$ or $Ru^{TEN}3$ was administered intraperitoneally when the tumor size reaching approximate 100 mm³. The LM3 xenograft-bearing mice were treated with $Ru^{TEN}1$ or $Ru^{TEN}3$ at the dose of 10 µM/Kg twice per week for 4 weeks. As illustrated in FIG. 7, $Ru^{TEN}1$ and $Ru^{TEN}3$ at 10 µM/Kg independently suppressed hepatocellular carcinoma LM3 tumor volume by more than 80% on day 28. Further, at all the doses that were tested, neither $Ru^{TEN}1$ nor $Ru^{TEN}3$ had caused lost in body weight, which indicated low toxicity of $Ru^{TEN}1$ and $Ru^{TEN}3$ (FIG. 8).

4.4 $Ru^{TEN}3$ Effectively Suppressed the Breast Cancer MD-MBA-231 Xenografts

The $Ru^{TEN}3$ of Example 1 were used in the present example to investigate its therapeutic efficacy on nude mice bearing human MD-MBA-231 breast cancer xenografts according to similar procedures described in Example 4.3. Results are depicted in FIGS. 9 to 11.

Figure 9:
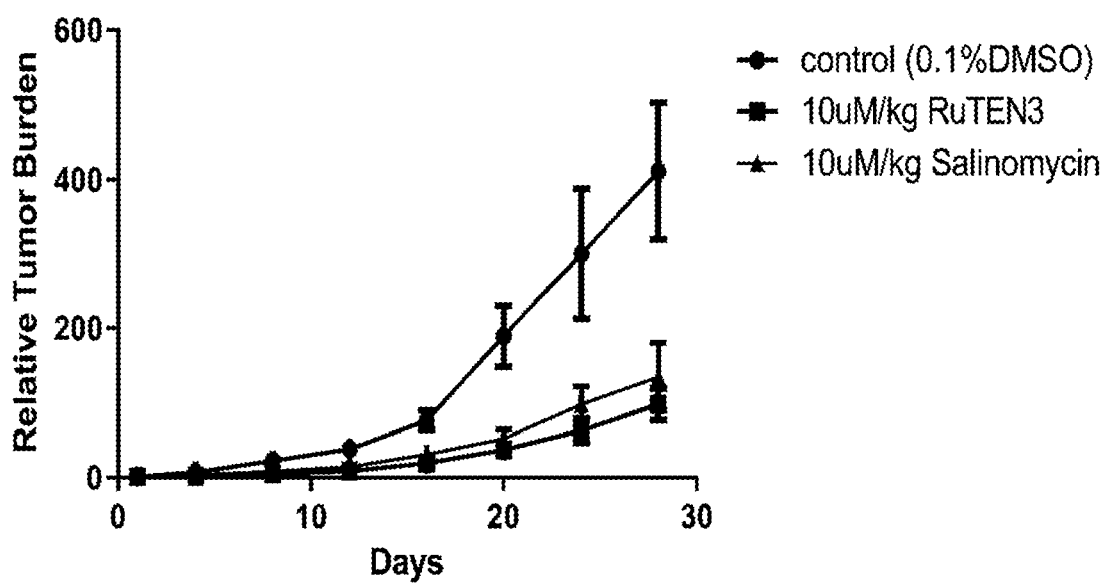
FIG. 9 are line graphs depicting the time course of the effect of $Ru^{TEN}3$ or salinomycin on tumor burden in breast cancer MDA-MB-231 tumor-bearing mice in accordance with one embodiment of the present disclosure.
Figure 10:
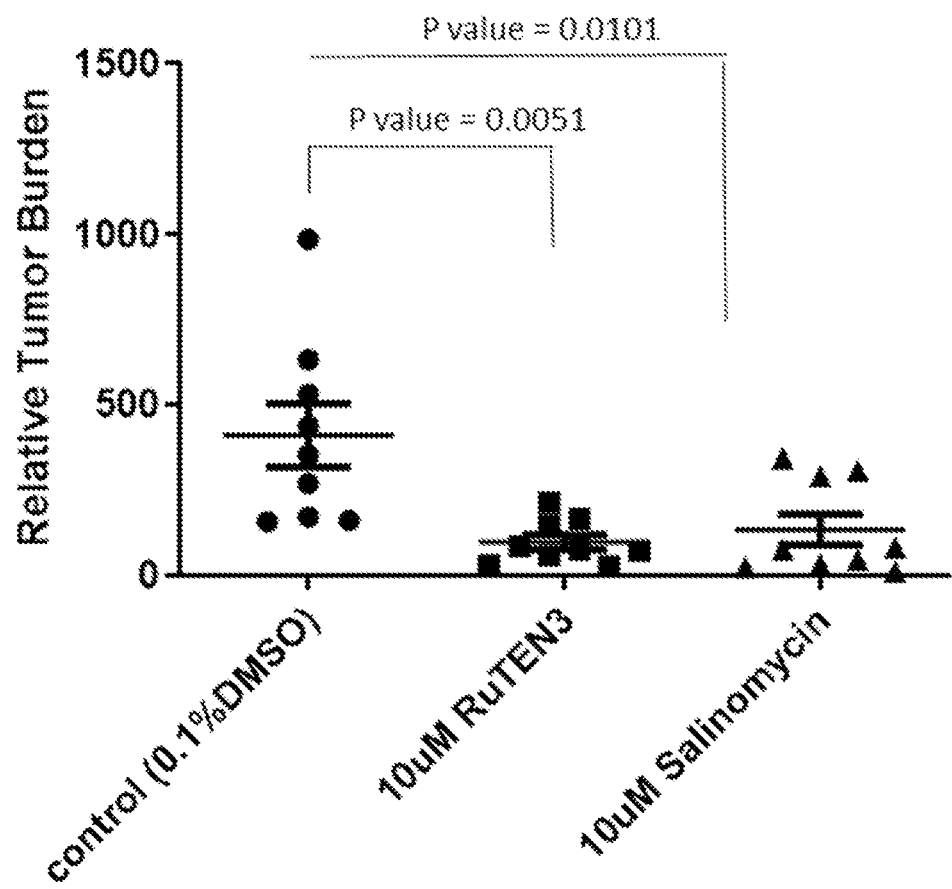
FIG. 10 depicts the effect of $Ru^{TEN}3$ on the tumor volume of breast cancer MDA-MB-231 in tumor-bearing mice in accordance with one embodiment of the present disclosure.
Figure 11:
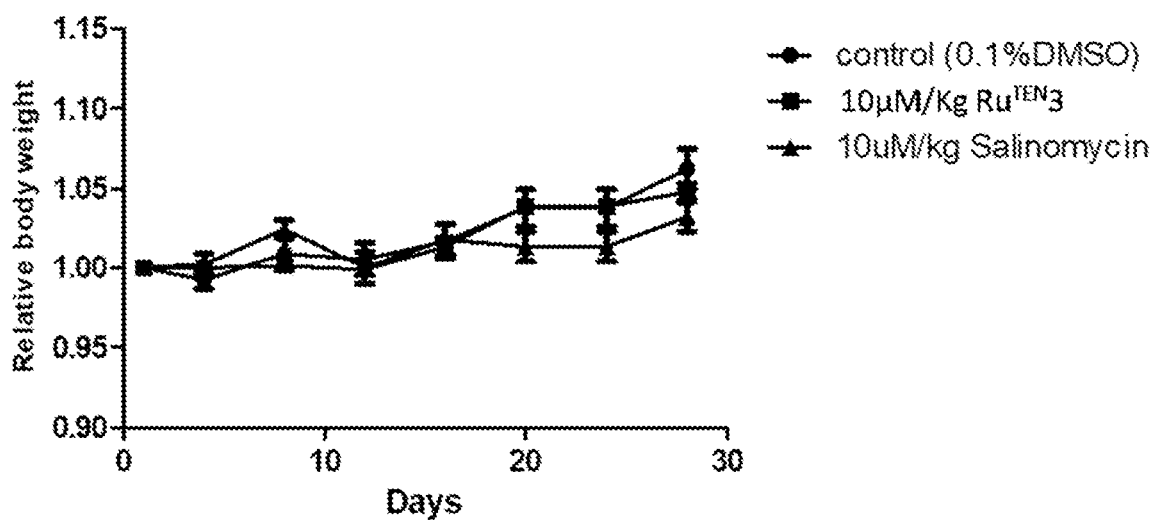
FIG. 11 depicts the effect of $Ru^{TEN}3$ on body weight of the breast cancer MDA-MB-231 tumor-bearing mice of FIG. 10.

As illustrated in FIGS. 9 and 10, $Ru^{TEN}3$ at the dose of 10 µM/Kg was as effective as salionmycin in suppressing the xenografted breast cancer volume by more than 75% on day 28. At the doses that was tested, neither $Ru^{TEN}3$ nor had caused lost in body weight, which indicated low toxicity of $Ru^{TEN}3$ and salinomycin (FIG. 11).

Disclosed herein is the use of ruthenium compounds, such as $Ru^{TEN}3$, with reduced toxicity and marked activity against TNBC, characterized by inhibition of invasive properties of breast cancer cells, killing of highly tumorigenic CD44+/CD24− cell subpopulation and notable activity against breast cancer in vivo. Targeting the subpopulation that are resistant to standard chemotherapeutic drugs may result in improved anticancer activity of $Ru^{TEN}$ complexes, as disclosed herein, in comparison with some known anticancer drugs. For example, highly toxic platinum drugs may result in serious side-effects in cancer patients, while $Ru^{TEN}$ complexes such as $Ru^{TEN}3$ may facilitate the development of less toxic chemotherapeutic regimens.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of the present disclosure.

What is claimed is:

1. A compound of formula (I), a solvate or a stereoisomer thereof,

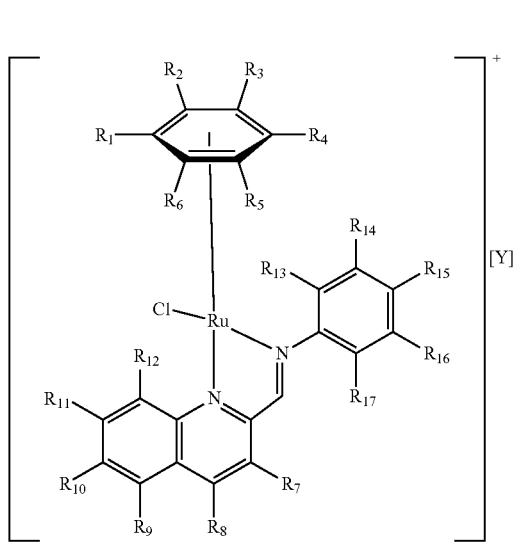

(I)

wherein, $R_1$, $R_3$, and $R_5$ are independently H;

$R_2$, $R_4$, and $R_6$ are independently isopropyl;

$R_7$, $R_8$, $R_9$, $R_{10}$, $R_{11}$, and $R_{12}$ are independently H, alkyl, alkoxyl, or halo;

$R_{13}$, $R_{14}$, and $R_{17}$ are independently H, alkyl, alkoxyl, hydroxy, halo, —C(=NH)NH$_2$, —SO$_3$H, —SO$_2$NH$_2$, —NR'R", or —CONH$_2$;

$R_{15}$ is H, hydroxy, halo, —C(=NH)NH$_2$, —SO$_3$H, —SO$_2$NH$_2$, or —CONH$_2$;

$R_{16}$ is H, alkyl, alkoxyl, hydroxy, —C(=NH)NH$_2$, —SO$_3$H, —SO$_2$NH$_2$—, —NR'R", or —CONH$_2$;

$R_{13}$ and $R_{14}$ are taken together to form a benzene ring, while $R_{15}$, $R_{16}$, and $R_{17}$ are independently H, alkyl, alkoxyl, hydroxy, halo, —C(=NH)NH$_2$, —SO$_3$H, —SO$_2$NH$_2$, —NR'R", or —CONH$_2$; or $R_{14}$ and $R_{15}$ are taken together to form a benzene ring, while $R_{13}$, $R_{16}$, and $R_{17}$ are independently H, alkyl, alkoxyl, hydroxy, halo, —C(=NH)NH$_2$, —SO$_3$H, —SO$_2$NH$_2$, —NR'R", or —CONH$_2$;

R' and R" are independently H or alkyl;

the alkyl is optionally substituted with one or more halo or hydroxy; and

Y is a counter anion.

2. The compound of claim 1, wherein the counter anion is selected from the group consisting of chloride, bromide, iodine, acetate, ascorbate, benzoate, benzenesulfonate, butyrate, cyclopentanepropionate, dodecylsulfoate, ethanesulfonate, glucuronate, glucoheptonate, hemisulfate, heptonate, hexonate, 2-hydroxyethanesulfonate, lactate, laurate, lauryl sulfate, methanesulfonate, 2-naphthalenesulfonate, nicotinate, nitrate, oleate, palmitate, 3-phenylpropionate, picrate, pivalate, propionate, stearate, thiocyanate, toluenesulfonate, trifluoroacetate, tosylate, undecanoate, and valerate.

3. A method for treating malignant neoplasm in a subject comprising administering to the subject a therapeutically effective amount of the compound of claim 1.

4. The method of claim 3, wherein the counter anion is selected from the group consisting of chloride, bromide, iodine, acetate, ascorbate, benzoate, benzenesulfonate, butyrate, cyclopentanepropionate, dodecylsulfoate, ethanesulfonate, glucuronate, glucoheptonate, hemisulfate, heptonate, hexonate, 2-hydroxyethanesulfonate, lactate, laurate, lauryl sulfate, methanesulfonate, 2-naphthalenesulfonate, nicotinate, nitrate, oleate, palmitate, 3-phenylpropionate, picrate, pivalate, propionate, stearate, thiocyanate, toluenesulfonate, trifluoroacetate, tosylate, undecanoate, and valerate.

5. The method of claim 3, wherein the malignant neoplasm is selected from the group consisting of carcinoma, sarcoma, lymphoma, leukemia, germ cell tumor, blastoma, brain cancer, medulloblastoma, glioma, head and neck cancer, oral cancer, laryngeal cancer, nasopharynx cancer, thyroid cancer, myeloid neoplasm, lung cancer, non-small cell lung cancer, small cell lung cancer, mesothelioma, hepatocellular carcinoma, lymphoid neoplasm, bone cancer, Ewing sarcoma, osteosarcoma, skeletal cancer, muscle cancer, rhabdomyo sarcoma, skin cancer, basal cell carcinoma, squamous cell carcinoma, connective tissue cancer, fibrosarcoma, cartilage cancer, chondrosarcoma, nerve tissue cancer, neuroblastoma, gastric cancer, esophageal cancer, pancreatic cancer, kidney cancer, bladder cancer, prostate cancer, breast cancer, triple-negative breast cancer, testicular cancer, ovarian cancer, uterine cancer, fallopian tube cancer, and cervical cancer.

6. The method of claim 5, wherein the breast cancer is a triple-negative breast cancer.

7. The method of claim 6, wherein the breast cancer is resistant to a hormone-based chemotherapeutic agent, an antibody-based chemotherapeutic agent, a platinum-based chemotherapeutic agent or a combination thereof.

8. The method of claim 3, wherein the malignant neoplasm is a metastatic malignant neoplasm.

9. The method of claim 3, wherein the subject is a human.

* * * * *

UNITED STATES PATENT AND TRADEMARK OFFICE
CERTIFICATE OF CORRECTION

PATENT NO. : 11,958,869 B2
APPLICATION NO. : 17/720110
DATED : April 16, 2024
INVENTOR(S) : Maria Babak et al.

Page 1 of 1

It is certified that error appears in the above-identified patent and that said Letters Patent is hereby corrected as shown below:

In the Claims

Column 31, Claim 1, Line 48, cancel the text beginning with "$R_{16}$ is H," to and ending "or -$CONH_2$;" in Column 31, Claim 1, Line 49, and insert the following:
--$R_{16}$ is H, alkyl, alkoxyl, hydroxy, -C(=NH)$NH_2$ , -$SO_3$ H, -$SO_2$ $NH_2$, -NR'R", or -$CONH_2$ ;--

Signed and Sealed this
Fifteenth Day of October, 2024

Katherine Kelly Vidal
*Director of the United States Patent and Trademark Office*